United States Patent [19]
Hickey et al.

[11] Patent Number: 6,071,899
[45] Date of Patent: Jun. 6, 2000

[54] AZETIDINONE DERIVATIVES FOR THE TREATMENT OF ATHEROSCLEROSIS

[75] Inventors: Deirdre Mary Bernadette Hickey, Saffron Walden, United Kingdom; Dashyant Dhanak, West Chester, Pa.; Colin Andrew Leach, Roydon; Robert John Ife, Stevenage, both of United Kingdom; David Graham Tew, Audubon, Pa.

[73] Assignee: SmithKline Beecham p.l.c., Brentford, United Kingdom

[21] Appl. No.: 08/836,085

[22] PCT Filed: Oct. 25, 1995

[86] PCT No.: PCT/EP95/04202

§ 371 Date: Sep. 30, 1997

§ 102(e) Date: Sep. 30, 1997

[87] PCT Pub. No.: WO96/13484

PCT Pub. Date: May 9, 1996

[30] Foreign Application Priority Data

Oct. 29, 1994 [GB] United Kingdom ............... 9421816

[51] Int. Cl.[7] ............... C07D 205/09; A61K 31/395
[52] U.S. Cl. ............... 514/210; 540/359; 540/360
[58] Field of Search ............... 540/359, 360; 514/210

[56] References Cited

U.S. PATENT DOCUMENTS

| | | | |
|---|---|---|---|
| 4,206,120 | 6/1980 | Hunt | 540/360 |
| 4,244,965 | 1/1981 | Howarth | 540/360 |
| 5,108,747 | 4/1992 | Pfaendler | 514/275 |

FOREIGN PATENT DOCUMENTS

| | | |
|---|---|---|
| 0 069 378 | 12/1983 | European Pat. Off. . |
| 0 115 308 | 8/1984 | European Pat. Off. . |
| 2 477 547 | 11/1981 | France . |

OTHER PUBLICATIONS

Beckwith, J. Org. Chem 53, 4339, 1988.
Bentley, Tet. Letters 1979, 391.
Arrowsmith, Tet. Letter 23, p. 357, 1982.
Beckwith, J. Org. Chem. 53, 4339, 1988.
Tanaka Tetrahedron Letters, vol. 23. No. 10. pp. 1075–1078, 1982 Oxford GB.

*Primary Examiner*—Mark L. Berca
*Attorney, Agent, or Firm*—James M. Kanagy; Charles M. Kinzig

[57] ABSTRACT

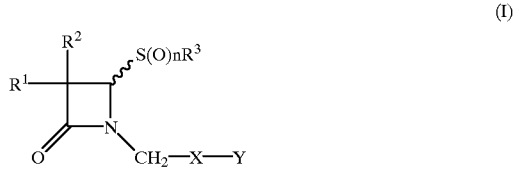

Azetidinone derivatives of formula (I) in which $R^1$ and $R^2$, which may be the same or different, is each selected from hydrogen or $C_{(1-8)}$alkyl; $R^3$ is $C_{(1-8)}$alkyl or $C_{(3-8)}$cycloalkyl each of which may be optionally substituted; X is a linker group; Y is an aryl group; and n is 0, 1 or 2; and excluding benzyl (4-methylthio-2-oxo-azetidin-1-yl)acetate are inhibitors of the enzyme Lp PLA2 and are of use in therapy, in particular treating atherosclerosis.

13 Claims, No Drawings

AZETIDINONE DERIVATIVES FOR THE TREATMENT OF ATHEROSCLEROSIS

This application is a 371 of PCT/EP95/04202, filed Oct. 25, 1995.

The present invention relates to certain novel monocyclic β-lactam compounds, processes for their preparation, intermediates useful in their preparation, pharmaceutical compositions containing them and their use in therapy, in particular in the treatment of atherosclerosis.

Lipoprotein Associated Phospholipase $A_2$ ($Lp$-$PLA_2$) was formerly known Platelet Activating Factor Acetyl Hydrolase (PAF acetyl hydrolase). The sequence of the enzyme, the isolation and purification thereof, isolated nucleic acids encoding the enzyme, recombinant host cells transformed with DNA encoding the enzyme are described in patent application WO 95/00649 (SmithKline Beecham plc). Suggested therapeutic uses for inhibitors of the enzyme included atherosclerosis, diabetes, rheumatoid arthritis, stroke, myocardial infarction, reperfusion injury and acute and chronic inflammation. A later patent application (WO 95/09921, Icos Corporation) and a related publication in Nature (Tjoelker et al, vol 374, Apr. 6, 1995, 549) describe the same enzyme and suggest that it may have potential as a therapuetic protein for regulating pathological inflammatory events.

It has been shown that $Lp$-$PLA_2$ is responsible for the conversion of phosphatidylcholine to lysophosphatidylcholine, during the conversion of low density lipoprotein (LDL) to its oxidised form. The enzyme is known to hydrolyse the sn-2 ester of oxidised phosphatidylcholine to give lysophosphatidylcholine and an oxidatively modified fatty acid. Both products of $Lp$-$PLA_2$ action are biologically active with lysophosphatidylcholine, a component of oxidised LDL, known to be a potent chemoattractant for circulating monocytes. As such, lysophosphatidylcholine is thought play a significant role in atherosclerosis by being responsible for the accumulation of cells loaded with cholesterol ester in the arteries. Inhibition of the $Lp$-$PLA_2$ enzyme would therefore be expected to stop the build up of these macrophage enriched lesions (by inhibition of the formation of lysophosphatidylcholine and oxidised free fatty acids) and so be useful in the treatment of atherosclerosis.

The increased lysophosphatidylcholine content of oxidatively modified LDL is also thought to be responsible for the endothelial dysfunction observed in patients with atherosclerosis. Inhibitors of $Lp$-$PLA_2$ could therefore prove beneficial in the treatment of this phenomenon. An $Lp$-$PLA_2$ inhibitor could also find utility in other disease states that exhibit endothelial dysfunction including diabetes, hypertension, angina pectoris and after ischaemia and reperfusion.

$Lp$-$PLA_2$ inhibitors may also have a general application in any disorder that involves lipid peroxidation in conjunction with $Lp$-$PLA_2$ activity to produce the two injurious products, lysophosphatidylcholine and oxidatively modified fatty acids. Such conditions include the aforementioned conditions atherosclerosis, diabetes, rheumatoid arthritis, stroke, myocardial infarction, reperfusion injury and acute and chronic inflammation. Further such conditions include various neuropsychiatric disorders such as schizophrenia (see Psychopharmacology Bulletin, 31, 159–165, 1995).

We have now identified a series of compounds which have been found to act as inhibitors of $Lp$-$PLA_2$.

Accordingly, the present invention provides a compound of formula (I):

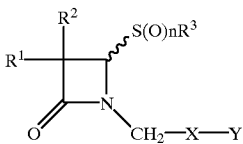

in which:
$R^1$ and $R^2$, which may be the same or different, is each selected from hydrogen or $C_{(1-8)}$alkyl;
$R^3$ is $C_{(1-8)}$alkyl, $C_{(3-8)}$cycloalkyl or $C_{(3-8)}$cycloalkyl$C_{(1-6)}$alkyl each of which may be optionally substituted;
X is a linker group;
Y is an aryl group; and
n is 0, 1 or 2; and
excluding benzyl (4-methylthio-2-oxo-azetidin-1-yl)acetate.

Compounds of formula (1) are inhibitors of $Lp$-$PLA_2$ and as such are expected to be of use in treating atherosclerosis and the other disease conditions noted above.

Suitably, $R^1$ and $R^2$ is each selected from hydrogen, methyl or ethyl. Preferably, $R^1$ and $R^2$ is each hydrogen or one of $R^1$ and $R^2$ is hydrogen and the other of $R^1$ and $R^2$ is methyl (to give a trans-methyl). More preferably, $R^1$ and $R^2$ is each hydrogen.

Representative examples of $R^3$ include methyl, ethyl, propyl, n-butyl, t-butyl and n-hexyl, cyclohexyl and cyclohexyl methyl. Suitable substituents for the alkyl or cycloalkyl group in $R^3$ include halo, hydroxy, and $CO_2R$ in which R is hydrogen, $C_{(1-8)}$alkyl, $C_{(2-8)}$alkenyl or an in vivo hydrolysable ester group. Preferably, the substituent is hydroxy or $CO_2R$. More preferably, the substituent is $CO_2R$ in which R is hydrogen or an in vivo hydrolysable ester group. Preferably, $R^3$ is an unsubstituted n-butyl, t-butyl or n-hexyl group or a $C_{(1-8)}$alkyl substituted by $CO_2R$ in which R is hydrogen or an in vivo hydrolysable ester group.

Preferably n is 1 or 2, more preferably 1.

Suitably X is a direct bond; a group X'$(CH_2)$m in which X' is CO, $CONR^5$, COO or CONHO in which $R^5$ is hydrogen or $C_{(1-6)}$alkyl and m is 0 or an integer from 1 to 12; or a $C_{(1-12)}$alkylene chain optionally interupted by X'. Preferably, X is a direct bond or a group X'$(CH_2)_m$. Preferably, X' is CO or $CONR^5$, more preferably CONH. Preferably, m is 1, 5, 6 or 7, preferably 6. Preferably, X is $CONH(CH_2)_6$.

Suitably, Y is a benzene ring, optionally substituted by up to three further substituents. Suitable substituents include halo and $C_{(1-8)}$alkyl. Preferably, Y is phenyl optionally substituted by halo.

It will be readily appreciated by the skilled person that C-4 of the β-lactam ring is a chiral centre which will give rise to the presence of stereoisomers. The present invention encompasses all such stereoisomers.

It will be further readily appreciated by the skilled person that, in compounds of formula (I) in which n is 1, that is sulphoxide compounds, the presence of the SO moiety will introduce an additional chiral centre into the molecule and therefore give rise to the existence of extra stereoisomers. The present invention encompasses all such stereoisomers.

In preferred compounds of formula (I), the absolute configurations at C-4 and the SO moiety are R and S respectively.

When used herein, the term 'alkyl' includes all straight chain and branched isomers. Representative examples thereof include methyl, ethyl, n-propyl, iso-propyl, n-butyl, sec-butyl, iso-butyl, t-butyl, n-pentyl and n-hexyl. Examples of cycloalkyl include cyclopropyl, cyclobutyl, cyclopentyl, cyclohexyl, cycloheptyl and cyclooctyl.

Suitable substituents for a ($C_{1-8}$)alkyl or ($C_{3-8}$)cycloalkyl group include, for example, halogen, cyano, azido, nitro, carboxy, ($C_{1-6}$)alkoxycarbonyl, carbamoyl, mono- or di-($C_{1-6}$)alkylcarbamoyl, sulpho, sulphamoyl, mono- or di-($C_{1-6}$)alkylsulphamoyl, amino, mono- or di-($C_{1-6}$)alkylamino, acylamino, ureido, ($C_{1-6}$)alkoxycarbonylamino, 2,2,2-trichloroethoxycarbonylamino, aryl, heterocyclyl, hydroxy, ($C_{1-6}$)alkoxy, acyloxy, oxo, acyl, 2-thienoyl, ($C_{1-6}$)alkylthio, ($C_{1-6}$)alkylsulphinyl, ($C_{1-6}$)alkylsulphonyl, hydroxyimino, ($C_{1-6}$)alkoxyimino, hydrazino, hydrazono, benzohydroximoyl, guanidino, amidino and iminoalkylamino.

When used herein, the term 'aryl' includes, unless otherwise defined, phenyl or naphthyl optionally substituted with up to five, preferably up to three substituents.

Suitable substituents for an aryl group include, for example, halogen, cyano, ($C_{1-6}$)alkyl, ($C_{3-7}$)cycloalkyl, ($C_{1-6}$)alkoxy, halo($C_{1-6}$)alkyl, hydroxy, amino, mono- or di-($C_{1-6}$)alkylamino, acylamino, nitro, carboxy, ($C_{1-6}$)alkoxycarbonyl, ($C_{1-6}$)alkoxycarbonyl($C_{1-6}$)alkyl, ($C_{1-6}$)alkylcarbonyloxy, carboxy($C_{1-6}$)alkyloxy, ($C_{1-6}$)alkylcarbonyloxy, ($C_{1-6}$)alkylthio, ($C_{1-6}$)alkylsulphinyl, ($C_{1-6}$)alkylsulphonyl, sulphamoyl, mono- and di-($C_{1-6}$)-alkylsulphamoyl, carbamoyl, mono- and di-($C_{1-6}$) alkylcarbamoyl, and heterocyclyl. Suitable examples include, for instance, bromo, chloro, fluoro methoxy, hydroxy and methyl.

When used herein, the terms 'halogen' and 'halo' include fluorine, chlorine, bromine and iodine and fluoro, chloro, bromo and iodo, respectively.

Examples of suitable pharmaceutically acceptable in vivo hydrolysable ester groups include those which break down readily in the human body to leave the parent acid or its salt. Suitable ester groups of this type include those of part formula (a), (b), (c), (d), (e) and (f):

 (a)

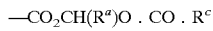 (b)

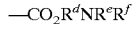 (c)

 (d)

(e)
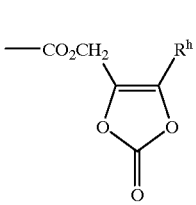

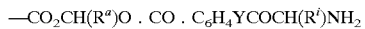 (f)

in which:
$R^a$ is hydrogen, ($C_{1-6}$)alkyl, ($C_{3-7}$)cycloalkyl, methyl, or phenyl;
$R^b$ is ($C_{1-6}$)alkyl, ($C_{1-6}$)alkoxy($C_{1-6}$)alkyl, phenyl, benzyl, ($C_{3-7}$)cycloalkyl, ($C_{1-6}$)alkyl($C_{3-7}$)cycloalkyl, 1-amino ($C_{1-6}$)alkyl, or 1-($C_{1-6}$alkyl)amino($C_{1-6}$)alkyl; or
$R^a$ and $R^b$ together form a 1,2-phenylene group optionally substituted by one or two methoxy groups;
$R^c$ is ($C_{1-6}$)alkyl, ($C_{3-7}$)cycloalkyl, ($C_{1-6}$)alkyl($C_{3-7}$) cycloalkyl;
$R^d$ is ($C_{1-6}$)alkylene optionally substituted with a methyl or ethyl group;

$R^e$ and $R^f$ which may be the same or different is each ($C_{1-6}$)alkyl;
$R^g$ is ($C_{1-6}$)alkyl;
$R^h$ is hydrogen, ($C_{1-6}$)alkyl or phenyl;
$R^i$ is hydrogen or phenyl optionally substituted by up to three groups selected from halogen, ($C_{1-6}$)-alkyl, or ($C_{1-6}$)alkoxy; and
Y is oxygen or NH.

Examples of suitable pharmaceutically acceptable in vivo hydrolysable ester groups include, for example:

(a) acyloxyalkyl groups such as acetoxymethyl, isobutyryloxymethyl, pivaloyloxymethyl, benzoyloxymethyl, α-acetoxyethyl, α-pivaloyloxyethyl, 1-(cyclohexylcarbonyloxy)ethyl, and (1-aminoethyl) carbonyloxymethyl;

(b) alkoxy/cycloalkoxycarbonyloxyalkyl groups, such as ethoxycarbonyloxymethyl and cyclohexyloxycarbonyloxymethyl and α-ethoxycarbonyloxyethyl;

(c) dialkylaminoalkyl especially di-loweralkylamino alkyl groups such as dimethylaminomethyl, dimethylaminoethyl, diethylaminomethyl or diethylaminoethyl;

(e) lactone groups such as phthalidyl and dimethoxyphthalidyl; and (f) (5-methyl-2-oxo-1,3-dioxolen-4-yl)methyl.

Preferred compounds of formula (I) include:
4-n-Butylsulfinyl-1-(4-phenyl-2-oxobutyl)azetidin-2-one;4-tert-Butylsulfinyl-1-(4-phenyl-2-oxobutyl)azetidin-2-one;4-n-Hexylsulfinyl-1-(4-phenyl-2-oxobutyl)azetidin-2-one;N-6-Phenylhexyl-(4-methylsulphinyl-2-oxoazetidin-1-yl)acetamide;

trans-N-(6-phenylhexyl )-(3-methyl-4-methylsulphinyl-2-oxoazetidin-1-yl)acetamide;4-Methylsulfinyl-1-(4-phenylbutyl)-azetidin-2-one; N-(6-Phenylhexyl )-(4-n-hexylsulfinyl-2-oxoazetidin-1-yl )acetamide; 4-(2-Hydroxyethylsulphinyl)-N-(4-phenyl-2-oxobutyl) azetidin-2-one (Diastereoisomer 2);
N-[6-(4-Fluorophenyl)hexyl]-[4-(3-allyloxycarbonylpropyl)sulphinyl -2-oxo-azetidin-1-yl]-acetamide (Diastereomer 2); N-[6-(4-Fluorophenyl) hexyl]-[4-(3-carboxypropyl)sulphinyl-2-oxo-azetidin-1-yl]-acetamide (Diastereoisomer 2);
N-[6-(4-Fluorophenyl)hexyl]-[4-carbemethoxymethylsulphinyl-2-oxo-azetidin-1-yl]-acetamide (Diastereomer 2); and
N-[6-(4-Fluorophenyl)hexyl]-[4-carboxymethylsulphinyl-2-oxo-azetidin-1-yl]-acetamide (Diastereoisomer 2).

Since the compounds of the present invention, in particular compounds of formula (I), are intended for use in pharmaceutical compositions, it will be understood that they are each provided in substantially pure form, for example at least 50% pure, more suitably at least 75% pure and preferably at least 95% pure (% are on a wt/wt basis). Impure preparations of the compounds of formula (I) may be used for preparing the more pure forms used in the pharmaceutical compositions. Although the purity of intermediate compounds of the present invention is less critical, it will be readily understood that the substantially pure form is preferred as for the compounds of formula (I). Preferably, whenever possible, the compounds of the present invention are obtained in crystalline form.

When some of the compounds of this invention are allowed to crystallise or are recrystallised from organic solvents, solvent of crystallisation may be present in the crystalline product. This invention includes within its scope such solvates. Similarly, some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation. In addition, different crystallisation conditions may lead to the formation of different polymorphic forms of crystalline products. This invention includes within its scope all polymorphic forms of the compounds of formula (I).

Compounds of the present invention are inhibitors of the enzyme lipoprotein associated phospholipase $A_2$ (Lp-PLA$_2$) and as such are expected to be of use in therapy, in particular in the treatment of atherosclerosis. In a further aspect therefore the present invention provides a compound of formula (I) for use in therapy.

The compounds of formula (I) are inhibitors of lysophosphatidylcholine production by Lp-PLA$_2$ and may therefore also have a general application in any disorder that involves endothelial dysfunction, for example atherosclerosis, diabetes, hypertension, angina pectoris and after ischaemia and reperfusion. In addition, compounds of formula (I) may have a general application in any disorder that involves lipid peroxidation in conjunction with enzyme activity, for example in addition to conditions such as atherosclerosis and diabetes, other conditions such as rheumatoid arthritis, stroke, inflammatory conditions of the brain such as Alzheimer's Disease, various neuropsychiatric disorders such as schizophrenia, myocardial infarction, reperfusion injury, restenosis, acute and chronic inflammation and sepsis. Furthermore, Lp-PLA$_2$ inhibitors may also have a general application in any disorder that involves activated monocytes, macrophages or lymphocytes, as all of these cell types express Lp-PLA$_2$, for example psoriasis.

Compounds of the present invention may also be of use in treating the above mentioned disease states in combination with anti-hyperlipidaemic or anti-atherosclerotic or anti-diabetic or anti-anginal or anti-inflammatory or anti-hypertension agents. Examples of the above include cholesterol synthesis inhibitors such as statins, anti-oxidants such as probucol, insulin sensitisers, calcium channel antagonists, and anti-inflammatory drugs such as NSAIDs.

In therapeutic use, the compounds of the present invention are usually administered in a standard pharmaceutical composition. The present invention therefore provides, in a further aspect, pharmaceutical compositions comprising a compound of formula (I) and a pharmaceutically acceptable carrier.

Suitable pharmaceutical compositions include those which are adapted for oral or parenteral administration or as a suppository.

The compounds of formula (I) which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound of formula (I) in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of formula (I) which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule.

Each dosage unit for oral administration contains preferably from 1 to 500 mg (and for parenteral administration contains preferably from 0.1 to 25 mg) of a compound of the formula (I).

The daily dosage regimen for an adult patient may be, for example, an oral dose of between 1 mg and 1000 mg, preferably between 1 mg and 500 mg, or an intravenous, subcutaneous, or intramuscular dose of between 0.1 mg and 100 mg, preferably between 0.1 mg and 25 mg, of the compound of the formula (I), the compound being administered 1 to 4 times per day. Suitably the compounds will be administered for a period of continuous therapy, for example for a week or more.

Compounds of formula (I) may be prepared from convenient starting materials by adapting synthetic procedures well known in the art. A suitable process comprises treating an azetidone of formula (II):

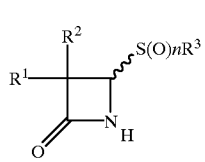

(II)

in which:
n, $R^1$, $R^2$ and $R^3$ are as hereinbefore defined;
with an alkylating agent of the formula (III):

ZCH$_2$XY    (III)

in which Z is a suitable leaving group such as halogen; and X and Y are as hereinbefore defined;
in the presence of a suitable base such as sodium hydride or potassium hydroxide, in a suitable alkylating solvent such as tetrahydrofuran (THF), and at a temperature in the range −10 to 0° C.

The preceding alkylation reaction is conveniently effected on compounds of formula (II) in which n is 0.

Compounds of formula (I) in which n is 1 or 2 can be readily prepared from compounds of formula (I) in which n is 0 by treatment thereof with a suitable oxidising agent such as m-chloroperbenzoic acid. Use of chiral oxidising agents such as (+)- or (−)-1,1'-bi-2-naphthol/titanium isopropoxide (N Komatsu et al, J Org Chem, 1993, 58, 7624–7626) can give diastereoisomeric selectivity, if not chirally pure compounds.

Compounds of formula (II) in which n is 0 may be obtained by treating 4-acetoxyazetidinone with a thiol $R^3SH$ in the presence of a base such as sodium ethoxide, in a suitable solvent such as ethanol at a temperature in the range 0 to 5° C.

Compounds of formula (III) may be readily prepared by adapting known synthetic procedures, according to the specific value of X. A convenient starting material is an appropriately substituted aryl compound which may then be elaborated to introduce the side chain $ZCH_2X$—.

Compounds of formula (I) in which X denotes a group $X'(CH_2)m$ in which X' denotes $CONR^5$ (amide) or CONHO (hydroxamate) may be conveniently prepared by treating an acid of the formula (IV):

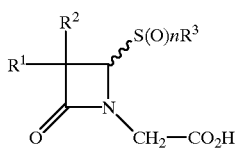

(IV)

in which:
n, $R^1$, $R^2$ and $R^3$ are as hereinbefore defined;
with an amine of the formula (V):

$NHR_5(CH_2)_mY$ (V)

or hydroxylamine of the formula (VI):

$NHO(CH_2)_mY$ (VI)

in which Y and m are as hereinbefore defined, in the presence of an activating agent such as ethyl chloroformate or dicyclohexylcarbodiimide (DCC), in a suitable solvent such as chloroform or dimethyl formamide, at a temperature in the range –10 to 20° C.

An acid of formula (IV) may be obtained by treating a compound of formula (II) with a 2-bromoacetate ester, under alkylating conditions as hereinbefore described; followed by the hydrolysis of the thus formed intermediate ester using standard conditions.

Compounds of formula (I) in which X denotes a group $X'(CH_2)m$ in which X' denotes COO (ester) may be conveniently prepared by a transesterification reaction from another ester, in particular the methyl ester of formula (VII):

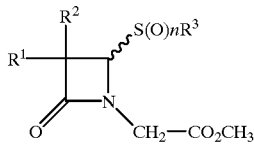

(VII)

in which:
n, $R^1$, $R^2$ and $R^3$ are as hereinbefore defined;
using conditions well known in the art for such reactions, for instance heating in toluene in the presence of a catalytic amount of sodium methoxide and an alcohol.

A compound of formula (VII) may be obtained by treating a compound of formula (II) with methyl 2-bromoacetate, under alkylating conditions as hereinbefore described.

Alternatively, a compound of formula (I) in which X denotes a group $X'(CH_2)m$ in which X' denotes COO (ester) may be prepared by treating a compound of formula (IV) with an alcohol $Y(CH_2)_mOH$ or an activated derivative thereof, for instance a tosylate.

Compounds of formula (I) in which in which R is an in vivo hydrolysable ester group may be readily prepared from coresponding compounds of formula (I) in which $R^3$ comprises a carboxy substituent by adapting procedures well known to those skilled in the art for ester pro-drug formation, for instance, treating the sodium salt with a suitable derivative of the pro-drug radical, under ester forming conditions.

Mixtures of diastereoisomeric compounds of formula (I) may be resolved, if so desired, according to procedures well known in the art, for instance sulphoxides (n=1) may be separated by chromatography and/or crystallisation. Chirally pure compounds may be prepared by chiral chromatography, from chirally pure intermediates or by chiral synthesis using chiral reagents or catalysis. Suitable chiral intermediates may be obtained by resolution, chiral induction or synthesis from natural chiral molecules, according to methods well known to those skilled in the art.

The present invention will now be illustrated by the following examples. In these, the terms 'diastereoisomer 1' and 'diastereoisomer 2' are used for sulfoxide compounds to refer to the diastereoisomers having R,R/S,S and R,S/S,R configurations, respectively. Such configurations were obtained initially by X-ray analysis of a limited number of compounds and then extrapolated to the remaning compounds on the basis of their $^1H$ nmr spectra. Unless otherwise specified, all compounds are racemic. Chiral compounds are described as 4R or S, SR or S where the 4 describes the centre at the C4 position in the azetidinone and the S describes the sulfoxide centre.

EXAMPLE 1

4-Methylthio-1-(4-phenyl-2-oxobutyl)azetidin-2-one

A solution of 4-methylthioazetidin-2-one (Clauss K, Grimm D, Prossel G, Anal, 1974, 539) (1.17 g, 0.01 mol) in THF (10ml) was added dropwise over 5 minutes to a suspension of sodium hydride (0.42 g, 0.01 mol) in dry THF (30 ml) under a nitrogen atmosphere at –10° C. The mixture was stirred for 15 minutes whilst keeping the temperature between –5 and –10° C. 1-Bromo-4-phenylbutan-2-one (Tetrahedron, 1970, 26, 5611) (2.27 g, 0.01 mol) in dry THF (10 ml) was added over 5 minutes at –10° C. The resultant mixture was stirred at room temperature for 1 hour then poured onto ice/water (100 g), filtered through Hyflo, washed with brine and separated. The organic extract was dried and evaporated under reduced pressure to a yellow oil. This was purified by flash chromatography on silica gel using petroleum ether/ethyl acetate 2:1, to give 4-methylthio-1-(4-phenyl-2-oxobutyl)azetidin-2-one as a colourless oil (1.08 g, 41%).
$^1H$ NMR (CDCl$_3$)δ:1.96 (3H, s, SCH$_3$), 2.73 (2H, t, J=7.0 Hz, CH$_2$Ph), 2.86 (2H, t, J=7.0 Hz, COCH$_2$), 2.97 (1H, dd, J=15.25, 2.25 Hz, H$_{3a}$), 3.37 (1H, dd, J=15.25, 5.00 Hz, H$_{3b}$), 3.68, 4.24 (1H each, d, J=18.5Hz, N—CH$_2$), 4.82 (1H, m, H$_4$), 7.10–7.31 (5H, m, Ph-H).
Found: C, 63.8; H, 6.3; N, 5.0% C$_{14}$H$_{17}$NO$_2$S requires: C, 63.9; H, 6.5; N, 5.3%

EXAMPLE 2

4-Methylsulphinyl-1-(4-phenyl-2-oxobutyl)azetidin-2-one

A solution of 4-methylthio-1-(4-phenyl-2-oxobutyl) azetidin-2-one (0.4 g, 1.5 mmol) in dichloromethane (40 ml) was cooled to –60° C. To this a solution of meta-chloroperbenzoic acid (m-CPBA, 0.52 g, 1.5 mmol) in dry dichloromethane (50 ml) was added dropwise over 10 minutes, maintaining the temperature between –50 and –60° C. The mixture was stirred at room temperature for 60 minutes, washed with dil. $Na_2SO_3$, dil. $NaHCO_3$, $H_2O$ (×2) and dried ($MgSO_4$). Evaporation under reduced pressure gave a residue which was purified by flash chromatography on silica gel using ethyl acetate then petroleum ether/ethyl acetate to give 4-methylsulphinyl-1-(4-phenyl-2-oxobutyl) azetidin-2-one as a waxy yellow solid (0.18 g, 43%). $^1H$ NMR demonstrated that this was a 1:1 mixture of diastereoisomers.

$^1H$ NMR ($CDCl_3$)δ:2.46 (3H, s, $SOCH_3$), 2.53 (3H, s, $SOCH_3$), 2.73 (4H, m, 2×$CH_2$-Ph), 2.70–2.90 (5H, m, 2×$COCH_3$, $H_{3a}$), 3.23 (1H, dd, J=14.75, 5.00 Hz, $H_{3b}$), 3.41 (1H, dd, J=14.75, 5.00 Hz, $H_{3b}$), 3.53 (1H, dd, J=14.75, 2.25 Hz, $H_{3a}$), 3.85, 4.22 (each 1H, J=19.00, 18.75 Hz,N—$CH_2$), 4.41, 4.49 (2H, dd, J=11.50, 11.75 Hz, N—$CH_2$), 4.69 (1H, m, $H_4$), 4.72 (1H, m, $H_4$), 7.15–7.32 (10H, m, 2×Ph-H).

Found: C, 59.2; H, 6.1; N, 4.9% $C_{14}H_{17}NO_3S$ requires: C, 60.2; H, 6.1; N, 5.0%

EXAMPLE 3

4-Methylsulphonyl-1-(4-phenyl-2-oxobutyl)azetidin-2-one

A solution of 4-methylthio-1-(4-phenyl-2-oxobutyl)azetidin-2-one (0.24 g, 0.9 mmol) in dichloromethane (30 ml) was cooled to –10° C. m-CPBA (1.10 g, 3.2 mmol) in dichloromethane (30 ml) was added dropwise over 10 minutes. This solution was stirred at room temperature for 90 minutes, washed with dil $Na_2SO_3$, dil $NaHCO_3$, water (×2), then dried ($MgSO_4$) and evaporated to an oil. This was purified by flash chromatography on silica gel using petroleum ether/ethyl acetate to give 4-methylsulphonyl-1-(4-phenyl-2-oxobutyl)azetidin-2-one as a colourless oil (0.14 g, 53%).

$^1H$ NMR ($CDCl_3$)δ:2.78 (2H, m, $CH_2Ph$), 2.90 (3H, s, $SO_2CH_3$), 2.96 (2H, m, $COCH_2$), 3.25 (1H, dd, J=15.5, 2.25 Hz, $H_{3a}$), 3.51 (1H, dd, J=15.5, 5.25 Hz, $H_{3b}$), 4.04, 4.40 (each 1H, d, J=18.25, 18.25 Hz, N—$CH_2$), 4.85 (1H, m, $H_4$), 7.15–7.33 (5H, m, Ph-H).

Found: C, 57.1; H, 5.8; N, 4.8% $C_{14}H_{17}NO_4S$ requires: C, 56.9; H, 5.8; N, 4.7%

EXAMPLE 4

4-Methylthio-1-(9-phenyl-2-oxononyl)azetidin-2-one

A. 1-Bromo-9-phenylnonan-2-one—A solution of 6-bromohexanoyl chloride (49.7 g, 0.233mol) in dry dichloromethane (40 ml) was added dropwise over 5 minutes to a suspension of aluminium chloride (31.0 g, 0.233 mol) in dry dichloromethane (100 ml), keeping the temperature between 20° C.–23° C. The mixture was stirred for 30 minutes at room temperature to give a yellow solution. Benzene (18.2 g, 0.233 mol) in dry dichloromethane (30 ml) was added and stirred for 20 hours at room temperature. Triethylsilane (59.9 g, 0.515 mol) was added over 10 minutes, maintaining the temperature between 25° C.–35° C. The solution was stirred for 60 minutes at room temperature. This was then poured onto ice/water (200g). A partial separation was achieved and the organic layer was washed with brine and water several times until the pH of the solution was neutral. The organic solution was dried ($MgSO_4$) and evaporated under reduced pressure to a yellow oil. This was distilled under reduced pressure at 90° C.–110° C./0.5 mbar to give colourless oils. The relevant fractions were combined and purified by flash chromatography on silica gel using hexane to give 6-bromo-1-phenylhexane as a colourless oil (18.33 g, 33%).

6-Bromo-1-phenylhexane (18.02 g, 0.075 mol) was dissolved in acetone (300 ml), NaI (44.85 g, 0.299 mol) was added, and the mixture heated at reflux temperature for 18 hours. This was filtered and the acetone evaporated under reduced pressure to give a residual mass which was extracted with n-pentane (150 ml). The insoluble solid was filtered off and the filtrate evaporated to give 6-iodo-1-phenylhexane as a colourless liquid (21.22 g, 99%).

6-Iodo-1-phenylhexane (17.43 g, 0.061 mol), acetyl acetone(6.66 g, 0.067) and potassium carbonate (8.41 g, 0.061 mol) were dissolved in dry absolute ethanol (75 ml) nd the solution was refluxed for 18 hours. After cooling to room temperature the solution was filtered and evaporated under reduced pressure to an oil. This was partitioned between ethyl acetate (80 ml) and water (80 ml), and the organic layer was washed with brine, dried and evaporated to an orange oil (15.27 g). This was purified by flash chromatography on silica gel using petroleum ether/ethyl acetate to give 9-phenylnonan-2-one as a colourless oil (7.12 g, 54%).

Bromine (5.21 g, 0.033 mol) was added to a solution of 9-phenylnonan-2-one (7.12 g, 0.033 mol) in dry methanol (75 ml) and stirred for 2 hours at room temperature. Water (50 ml) was added and stirring continued for 18 hours at room temperature. Ether (175 ml) and water (100 ml) were added, the organic layer washed with dil. $NaHCO_3$, water (×2), dried ($MgSO_4$) and evaporated under reduced pressure to an oil (5.39 g). Petroleum ether (40° C.–60° C., 50 ml) was added and the mixture cooled to –10° C. and filtered. The solid obtained was re-dissolved in ether (40 ml) and evaporated under reduced pressure to an oil (4.06 g) which was was further purified by flash chromatography on silica gel using hexane/ethyl acetate to give 1-bromo-9-phenylnonan-2-one a pale yellow solid (3.80 g, 39%).

B. 4-Methylthio-1-(9-phenyl-2-oxononyl)azetidin-2-one—Substituting 1-bromo-9-phenylnonan-2-one (1.9 g, 6.4 mmol) for 1-bromo-4-phenylbutan-2-one and using corresponding molar quantities of 4-methylthioazetidin-2-one and NaH by the method described in Example 1 gave 4-methylthio-1-(9-phenyl-2-oxononyl)azetidin-2-one as a yellow solid (1.09 g, 51%), m.p. 48° C.–51° C., after purification by flash chromatography on silica gel using petroleum ether/ethyl acetate as eluant.

$^1H$ NMR ($CDCl_3$)δ:1.23–1.44 (10H, m, 5×$CH_2$), 2.02 (3H, s, $SCH_3$), 2.41 (2H, t, J=7.25 Hz, $COCH_2$), 2.60 (2H, t, J=7.25Hz, $CH_2Ph$), 3.03 (1H, dd, J=15.0, 2.0 Hz, $H_{3a}$), 3.43 (1H, dd, J=15.00, 5.00 Hz, $H_{3b}$), 3.72, 4.29 (each 1H, d, J=18.5 Hz, N—$CH_2$), 4.92 (1H, m, $H_4$), 7.14–7.30 (5H, m, Ph-H).

Found: C, 67.9; H, 7.9; N, 4.1% $C_{19}H_{27}NO_2S$ requires: C, 68.4; H, 8.2; N, 4.2%

EXAMPLE 5

4-Methylsulphinyl-1-(9-phenyl-2-oxononyl)azetidin-2-one

EXAMPLE 6

4-Methylsulphonyl-1-(9-phenyl-2-oxononyl)azetidin-2-one

A solution of 4-methylthio-1-(9-phenyl-2-oxononyl)azetidin-2-one (0.993 g, 2.98 mmol) in dry dichloromethane (90 ml) was cooled to –50° C. and mCPBA (0.95 g, 2.58 mmol) in dry dichloromethane (50 ml) was added dropwise over 30 minutes, then stirred for 90 minutes at room temperature. This was washed with dil $Na_2SO_3$, dil $NaHCO_3$ and water (×2), dried ($MgSO_4$) and evaporated to a solid (1.09 g). This was purified by flash chromatography on silica gel eluted with petroleum ether/ethyl acetate 1 ethanol to give 4-methylsulphinyl-1-(9-phenyl-2-oxononyl)azetidin-2-one (Example 5) as a white waxy solid (0.718 g, 69%).
$^1$H NMR (CDCl$_3$)δ:1.23–1.65 (20H, m, 2×CH$_2$CH$_2$CH$_2$CH$_2$CH$_2$), 2.43 (4H, t, J=7.25 Hz, 2×COCH$_2$), 2.47 (3H, s, SOCH$_3$), 2.54 (3H, s, SOCH$_3$), 2.60 (4H, t, J=7.25 Hz, 2×CH$_2$Ph), 2.89 (1H, dd, J=15.0, 2.25 Hz, H$_{3a}$), 3.24 (1H, dd, J=14.75, 5.00 Hz, H$_{3b}$), 3.41 (1H, dd, J=15.0, 5.25 Hz, H$_{3b}$), 3.54 (1H, dd, J=14.75, 1.75 Hz, H$_{3a}$), 3.91, 4.51 (each 1H, d, J=19.0, 19.0 Hz, N—CH$_2$), 4.23, 4.44 (each 1H, d, J=19.0, 19.0 Hz, N—CH$_2$), 4.70 (1H, m, H$_4$), 4.81 (1H, m, H$_4$), 7.15–7.30 (10H, m, 2×Ph-H).
Found: C, 64.8; H, 7.7; N, 4.1% C$_{19}$H$_{27}$NO$_3$S requires: C, 65.3; H, 7.8; N, 4.0% and 4-methylsulphonyl-1-(9-phenyl-2-oxononyl)azetidin-2-one (Example 6) as a colourless solid (0.185 g, 17%, m.p. 81° C.–82° C.)
$^1$H NMR (CDCl$_3$)δ:1.18–1.52 (10H, m, CH$_2$CH$_2$CH$_2$CH$_2$CH$_2$), 2.33 (2H, t, J=7.25 Hz,COCH$_2$), 2.53 (2H, t, J=7.25 Hz, CH$_2$Ph), 2.87 (3H, s, SO$_2$CH$_3$), 3.18 (1H, dd, J=15.5, 2.25 Hz, H$_{3a}$), 3.46 (1H, dd, J=15.5, 5.25 Hz, H$_{3b}$), 4.00, 4.35 (each 1H, d, J=18.75, 18.75 Hz, N—CH$_2$), 4.80 (1H, m, H$_4$), 7.08–7.23 (5H, m, Ph-H).
Found: C,62.0; H, 7.3; N, 3.7% C$_{19}$H$_{27}$NO$_4$S requires: C, 62.4; H, 7.5; N, 3.8%

EXAMPLE 7

4-Methylthio-1-phenacyl-azetidin-2-one—

Substituting 2-bromoacetophenone (1.70 g, 8.54 mmol) for 1-bromo-4-phenylbutan-2-one and using corresponding molar quantities of 4 methylthioazetidin-2-one and NaH and using the method of Example 1, except that the 2-bromoacetophenone was added over 20 minutes at −55° C., gave 4-methylthio-1-phenacylazetidin-2-one as a yellow solid (0.62 g, 31%), m.p. 43° C.–45° C.
$^1$H NMR (CDCl$_3$)δ:2.04 (s, 3H, SCH$_3$), 3.07 (1H, dd, J=15.25, 1.75 Hz, H$_{3a}$), 3.50 (1H, dd, J=15.25, 5.0 Hz, H$_{3b}$), 4.32, 4.99 (each 1H, d, J=18.25, 8.25 Hz, N—CH$_2$), 5.03 (1H, m, H$_4$), 7.46–7.66, 7.91–7.95 (3H, 2H, m, Ph-H).
Found: C, 61.2; H, 5.8; N, 5.6% C$_{12}$H$_{13}$NO$_2$S requires: C, 61.2: H, 5.6; N, 5.9%

EXAMPLE 8

4-Methylsulphinyl-1-phenacylazetidin-2-one

EXAMPLE 9

4-Methylsulphonyl-1-phenacylazetidin-2-one

Substituting 4-methylthio-1-phenacyl-azetidin-2-one (0.53 g, 2.25 mmol) for 4-methylthio-1-(9-phenyl-2-oxononyl)azetidin-2-one and using corresponding molar quantities of mCPBA as for Examples 5 and 6 gave 4-methylsulphinyl-1-phenacylazetidin-2-one (Example 8) as a waxy white solid (0.45 g, 80%).
$^1$H NMR (CDCl$_3$)δ:2.50 (3H, s, SOCH$_3$), 2.58 (3H, s, SOCH$_3$), 2.98 (1H, dd, J=15.0, 2.50 Hz, H$_{3a}$), 3.32 (1H, dd, J=15.0, 5.0 Hz,H$_{3b}$), 3.50 (1H, dd, J=15.0, 5.25 Hz, H$_{3b}$), 3.63 (1H, dd, J=2.50, 15.0Hz, H$_{3a}$), 4.52, 5.20 (each 1H, d, J=18.75, 18.75 Hz, N—CH$_2$), 4.85, 5.12 (each 1H, d, J=18.75, 18.75 Hz, N—CH$_2$), 4.86 (1H, m, H$_4$), 4.95 (1H, m, H$_4$), 7.45–7.67, 7.86–7.93 (6H, 4H, m, Ph-H).
Found: C, 56.7; H, 5.2; N, 5.5% C$_{12}$H$_{13}$NO$_3$S requires: C, 56.9; H,5.2; N, 5.5% and 4-methylsulphonyl-1-phenacyl-azetidin-2-one (Example 9) as a yellow gum (0.09 g, 15%).
$^1$H NMR (CDCl$_3$)δ:2.98 (3H, s, SO$_2$CH$_3$), 3.34 (1H, dd, J=15.5, 2.0 Hz, H$_{3a}$), 3.58 (1H, dd, J=15.5, 5.25 Hz,H$_{3b}$), 4.68, 5.13 (each 1H, d, J=18.5, 18.5 Hz, N—CH$_2$), 5.04 (1H, m, H$_4$), 7.47–7.57, 7.88–7.91 (3H, 2H, m, Ph-H).
Found: C, 53.9; H, 5.0; N, 4.6% C$_{12}$H$_{13}$NO$_4$S requires: C, 53.9; H, 5.0; N, 5.1%

The compounds of Examples 10 to 15 were prepared by methods analogous to those described for Examples 1 to 9.

EXAMPLE 10

4-Methylthio-1-(5-phenyl-2-oxopentyl)azetidin-2-one

Colourless oil, 34% yield
Found: C, 59.3; H, 7.6; N, 3.0% C$_{15}$H$_{19}$NO$_2$S requires: C, 59.3; H, 7.3; N, 3.3%

EXAMPLE 11

4-Methylsulphinyl-1-(5-phenyl-2-oxopentyl)azetidin-2-one

Colourless solid, m.p. 62–64° C., 69.5% yield
Found: C, 61.0; H, 6.4; N, 4.7% C$_{15}$H$_{19}$NO$_3$S requires: C, 61.4; H, 6.5; N, 4.8%

EXAMPLE 12

4-Methylsulphonyl-1-(5-phenyl-2-oxopentyl)azetidin-2-one

Colourless solid, m.p. 62–64° C., 92% yield
Found: C, 58.0; H, 6.0; N, 4.7% C$_{15}$H$_{19}$NO$_4$S requires: C, 58.2; H, 6.2; N, 4.5%

EXAMPLE 13

4-Methylthio-1-(7-phenyl-2-oxoheptyl)azetidin-2-one

Yellow solid, m.p. 37–8° C., 50% yield
Found: C, 66.7; H, 7.4; N, 4.6% C$_{17}$H$_{23}$NO$_2$S requires: C, 66.9; H, 7.6; N, 4.6%

EXAMPLE 14

4-Methylsulphinyl-1-(7-phenyl-2-oxoheptyl)azetidin-2-one

Colourless oil, 54%
$^1$H NMR (CDCl$_3$)δ:1.34,1.62 (6H, 2×m,CH$_2$), 2.4 (2H, m, COCH$_2$), 2.47, 2.54 (3H, 2×s, SOCH$_3$), 2.61 (2H, t, J=7.7 Hz, CH$_2$Ph), 3.24, 3.53, 2.90, 3.40 (2H, 4×dd, J=15.5 Hz, H$_{3a}$, J=15.2 Hz, H$_{3a}$), 3.91, 4.49,4.22, 4.42 (2H, 4×d, J=19 Hz, N—CH$_2$), 4.80, 4.69 (1H, 2×m, H$_4$), 7.15–7.30 (5H,m,Ph-H)

EXAMPLE 15

4-Methylsulphonyl-1-(7-phenyl-2-oxoheptyl)azetidin-2-one

Colourless solid, m.p. 77–9 C, 17%
Found: C, 60.2; H, 6.7; N, 4.2; C$_{17}$H$_{23}$NO$_4$S requires: C, 60.5; H, 6.9; N, 4.2%

EXAMPLE 16

4-Butylthio-1-(4-phenyl-2-oxobutyl)azetidin-2-one

A. 4-Butylthioazetidin-2-one—Sodium (1.2 g, 0.05 mol) was dissolved in ethanol (100 ml), cooled, and butanethiol (4.7 g, 0.0525 mol) was added. The mixture was cooled to 5° C. and treated with a solution of 4-acetoxyazetidinone (6.46 g, 0.05 mol) in ethanol (50 ml). The mixture was stirred for 30 minutes and the bulk of the ethanol was evaporated. The residue was partitioned between ethyl acetate and water and the aqueous layer was extracted with ethyl acetate. The combined extracts were washed with brine, dried and evaporated. Flash chromatography (silica gel, ethyl acetate-hexane) gave the title compound as an oil (3.25 g, 41%).
$^1$H NMR (CDCl$_3$)δ:

B. 4-Butylthio-1-(4-phenyl-2-oxobutyl)azetidin-2-one—A mixture of 4-butylthioazetidin-2-one (3.2 g, 0.02 mol), tetrabutylammonium bromide (0.65 g, 0.002 mol), 1-bromo-4-phenyl-2-oxobutane (5.0 g, 0.022 mol) and powdered potassium hydroxide (1.23 g, 0.022 mol) was stirred in dry tetrahydrofuran (100 ml) for 30 minutes with some cooling from an ice bath. The mixture was partitioned between ethyl acetate-dilute ammonium chloride solution. The aqueous solution was extracted with ether (×2) and the combined extracts were washed with brine, dried and evaporated. Flash chromatography (silica gel, hexane-ethyl acetate) gave the title compound as a yellow oil (3.6 g, 59%).
$^1$H NMR (CDCl$_3$)δ:

EXAMPLE 17

4-Butylsul finyl-1-(4-phenyl-2-oxobutyl)azetidin-2-one, (>99% diastereoisomer 1)

A solution of m-chloroperbenzoic acid (0.81 g, 0.0047 moles) in dichloromethane (50 ml) was added dropwise to a stirred solution of 4-butylthio-N-(4-phenyl-2-oxobutyl) azetidin-2-one (1.2 g, 0.0039 moles) in dichloromethane (50 ml) at −60° C. Stirring continued at −60° C. for 30 minutes then the mixture was poured into an aqueous solution of sodium hydrogen carbonate and sodium sulphite. The layers were separated and the aqueous was extracted with dichloromethane. The combined extracts were dried and evaporated to give a solid which was slurried in ether, filtered, washed with ether and petrol. The solid was recrystallised from ether to give the title compound as white crystals, 280 mg (22%), mp 145–6° C.
Found: C, 62.19; H, 6.80; N, 4.28; C$_{17}$H$_{23}$NO$_3$S 0.3H$_2$O requires: C, 62.47; H, 7.28; N, 4.29.

EXAMPLE 18

4-Butylsulfinyl-1-(4-phenyl-2-oxobutyl)azetidin-2-one, (80% distereoisomer 2)

The mother liquors from the above preparation were concentrated and upon standing produced crystals. Recrystallisation from ether gave the title compound 84 mg (7%), mp 64–5° C.
Found: C, 62.11; H, 6.85; N, 4.30; C$_{17}$H$_{23}$NO$_3$S 0.3 H$_2$O requires: C, 62.47; H, 7.28; N, 4.29

EXAMPLE 19

4-Butylsulfonyl-1-(4-phenyl-2-oxobutyl)azetidin-2-one

A solution of m-chloroperbenzoic acid (1.5 g, 9 mmol) in dichloromethane (50 ml) was added to a stirred solution of 4-butylthio-1-(4-phenyl-2-oxobutyl)azetidin-2-one (0.9 g, 3 mmol) in dichloromethane (50 ml) at 0° C. The cooling bath was removed after 30 minutes and the mixture was stirred for a further 2 hours. The mixture was poured into an aqueous solution of sodium hydrogen carbonate and sodium sulphite. The layers were separated and the aqueous layer was extracted with dichloromethane. The combined organic extracts were washed with sodium hydrocen carbonate solution, dried (MgSO$_4$) and evaporated to give a solid which was slurried in ether, filtered, washed with ether and petrol. Recrystallisation from ether gave the title compound as a white solid, 530 mg, 43%, m.p. 93–94° C.
Found: C, 59.69; H, 6.61; N, 4.26; C$_{17}$H$_{23}$NO$_4$S 0.17H$_2$O requires: C, 59.96; H, 6.91; N, 4.11.

EXAMPLE 20

4-tert-Butylthio-1-(4-phenyl-2-oxobutyl)azetidin-2-one

Substituting 4-tert-butylthioazetidinone (Kaura et al, JCS Chem Comm, 1980, 34) (2.1 g, 13 mmol) for 4-butylthioazetidin-2-one and using corresponding molar proportions of the other reagents in Example 16B gave the title compound as a solid, 0.6 g, 16%, m.p. 65° C.
$^1$H NMR (CDCl$_3$)δ:1.29 (9H, s, t-Bu), 2.73 (2H, t, J=7 Hz, CH$_2$Ph). 2.88 (2H, t, J=7 Hz, COCH$_2$), 3.00 (1H, dd, J=2.5, 15 Hz, H$_{3a}$), 3.55 (1H, dd, J=5, 15 Hz, H$_{3b}$), 3.59, 4.32 (each 1H, d, J=17.5 Hz, NCH$_2$), 4.99 (1H, m, H$_4$), 7.16–7.32 (5H, m, Ph-H)

EXAMPLE 21

4-tert-Butylsulfinyl-1-(4-phenyl-2-oxobutyl) azetidin-2-one 4-tert-Butylthio-1-(4-phenyl-2-oxobutyl)azetidin-2-one (0.6 g, 2 mmol) was dissolved in dry dichloromethane (30 ml) and the solution cooled to −50° C. A solution of m-CPBA (0.32 g, 2 mmol) in dry dichloromethane (20 ml) was added dropwise and the resulting mixture stirred for an additional 3 h. The mixture was poured into an aqueous solution of sodium hydrogen carbonate and sodium sulphite. The layers were separated and the aqueous layer was extracted with dichloromethane. The combined organic extracts were washed with sodium hydrogen carbonate solution, dried (MgSO$_4$) and evaporated to give a solid which was purified by flash hromatography using ethyl acetate/ether and ethyl acetate as the eluting solvents. Evaporation of the appropriate fractions gave the title compound as a colourless solid, 0.3 g, 48%, m.p. 79–81° C.
Found: C, 63.6; H, 7.0; N, 4.5%; C$_{17}$H$_{23}$NO$_3$ requires: C, 63.5; H, 7.2; N, 4.4%

EXAMPLE 22

4-Hexylthio-N-(4-phenyl-2-oxobutyl)azetidin-2-one

A. 4-Hexylthioazetidinone—Substituting 1-hexanethiol (6.0 ml, 0.042 mol) for 1-butanethiol and using corresponding molar proportions of the other reagents in Example 16A gave the title compound as an oil, 6.97 g, 95%.
$^1$H NMR (CDCl$_3$)δ:

B. 4-Hexylthio-1-(4-phenyl-2-oxobutyl)azetidin-2-one—Substituting 4-hexylthioazetidinone (6.0 g, 0.032 moles) for 4-butylthioazetidin-2-one and using corresponding molar proportions of the other reagents in Example 16B gave the tilte compound as an oil (5.6 g, 52%).
$^1$H NMR (CDCl$_3$)δ:

EXAMPLE 23

4-Hexylsulfinyl-1-(4-phenyl-2-oxobutyl)azetidin-2-one, (>99% diastereoisomer 1)

A solution of m-chloroperbenzoic acid (2.48 g, 0.0144 mol) in dichloromethane (50 ml) was added dropwise to a stirred solution of 4-hexylthio-1-(4-phenyl-2-oxobutyl) azetidin-2-one (4.0 g, 0.012 mol) in dichloromethane (50 ml) at −60° C. Stirring was continued at −60° C. for 30 minutes then the mixture was poured into an aqueous solution of sodium hydrogen carbonate and sodium sulphite. The layers were separated and the aqueous was extracted with dichloromethane. The combined extracts were dried ($MgSO_4$) and evaporated to give a solid which was slurried in ether, filtered, washed with ether and petrol. The solid was recrystallised from ethyl acetate to give the title compound as white crystals, 920 mg, (22%), m.p. 154–5° C.
Found: C, 64.93; H, 7.50; N, 4.24; $C_{19}H_{27}NO_3S$ requires: C, 65.30; H, 7.79; N, 4.01.

EXAMPLE 24

4-Hexylsulfinyl-1-(4-phenyl-2-oxobutyl)azetidin-2-one, (97% diastereoisomer 2)

The mother liquors from the above preparation were concentrated and chromatographed (fine silica gel, ethyl acetate) to give the title compound which crystallised from ether as a white solid, 800 mg, (19%), mp 67–8° C.
Found: C, 64.67; H, 7.47; N, 4.30; $C_{19}H_{27}NO_3S$ 0.1$H_2O$ requires: C, 64.96; H, 7.80; N, 3.99.

EXAMPLE 25

Benzyl (4-methylthio-2-oxo-azetidin-1-yl)acetate

This compound was prepared as an off white waxy solid as described in Ref
$^1H$ NMR ($CDCl_3$)δ:2.01 (3H, s, $CH_3$), 3.03 (1H, ddd, J=15, 2.3,0.7 Hz, $H_{3b}$), 3.40 (1H, dd, J=15, 5 Hz, $H_{3a}$), 3.74, 4.30 (each 1H, d, J=18 Hz, $NCH_2$), 4.91 (1H, dd, J=2, 2.3 Hz, $H_4$), 5.16, 5.20 (each 1H, d, J=12 hz, $OCH_2$), 7.37, (SH, m, Ph-H)

Examples 26 and 27 were prepared by methods analogous to those described in Examples 2 and 3. Examples 26 and 27 were separated by crystallisation.

EXAMPLE 26

Benzyl (4-methylsulfinyl-2-oxo-azetidin-1-yl) acetate, (90% diastereoisomer 1)

$^1H$ NMR ($CDCl_3$)δ:2.56 (3H, s, $SOCH_3$), 2.91 (1H, dd, J=2.5, 15 Hz, $H_{3a}$), 3.37 (1H, dd, J=5.2, 15 Hz, $H_{3b}$), 4.20, 4.42 (each 1H, d, J=18 Hz, N—$CH_2$), 4.75 (1H, dd, J=2.5, 5.2 Hz, $H_4$), 5.18 (2H, m, $CH_2Ph$), 7.36 (5H, m, Ph-H)

EXAMPLE 27

Benzyl (4-methylsulfinyl-2-oxo-azetidin-1-yl)acetate 55% diastereoisomer 2

$^1H$ NMR ($CDCl_3$)δ:2.47 (3H, s, $SOCH_3$), 3.21 (1H, dd, J=5, 15 Hz, $H_{3a}$), 3.57 (1H, m, $H_{3b}$), 3.89, 4,49 (each 1H, d, J=18.5 Hz, N—$CH_2$), 4.76 (1H, dd, J=2.2, 5 Hz, $H_4$), 5.19 (2H, s, $CH_2Ph$), 7.37 (5H, m, Ph-H)

EXAMPLE 28

Benzyl (4-methylsulfonyl-2-oxo-azetidin-1-yl) acetate $^1H$ NMR ($CDCl_3$)δ:2.94 (3H, s, $SO_2CH_3$), 3.27 (1H, dd, J=2.2, 15.5 Hz, $H_{3a}$), 3.49 (1H, dd, J=5.2, 15.5 Hz, $H_{3b}$), 4.05, 4,41 (each 1H, d, J=18.5 Hz, N—$CH_2$), 4.89 (1H, dd, J=2.2, 5.2 Hz, $H_4$), 5.17, 5.22 (each 1H, d, J=12 Hz, $CH_2Ph$), 7.35 (5H, m, Ph-H)

EXAMPLE 29

(+)-Benzyl (4-methylthio-2-oxoazetidin-1-yl)acetate

A. (+)-(4-Methylthio-2-oxo-azetidin-1-yl)-acetic acid and (−)-(4-methylthio-2-oxo-azetidin-1-yl)-acetic acid—6.0g (0.034 mol) of (+)-(4-methylthio-2-oxo-azetidin-1-yl) acetic acid (E Hunt et al, Tet. Lett., 1979, 391) was dissolved in ethanol (50 ml) and the solution treated with a solution of brucine dihydrate (15.97 g, 0.034 mol) in ethanol (200 ml). The mixture was cooled and the resulting solid was filtered and recrystallised from ethanol. The solid was dissolved in water and the solution acidified with dilute hydrochloric acid to pH1.5. The resulting mixture was extracted with ether (2×100 ml), the organic phase separated, dried ($MgSO_4$), filtered and evaporated to give (−)-(4-methylthio-2-oxo-azetidin-1-yl)-acetic acid, 1.02 g, 35%, m.p. 112–1 13° C., $[\alpha]_{25}^D$=−109.5° (c=1, ETOH). The filtrate from the initial crystallization was evaporated to dryness, acidified to pH 1.5 with dilute hydrochloric acid and extracted with ether (2×100 ml). The combined ether extracts were dried ($MgSO_4$), filtered and evaporated to give (+)-(4-methylthio-2-oxo-azetidin-1-yl)-acetic acid, 1.14 g, 38%, m.p. 117–118° C., $[\alpha]_{25}^D$=+104.70 (c=1, EtOH).

B. (+)-Benzyl (4-methylthio-2-oxoazetidin-1-yl)acetate—3-benzoyl-3-phenyldiazirine (1.0 g 4.3 mmol) was dissolved in ether (25 ml) and a solution of NaOH (0.13 g, 3.4 mmol) in methanol/$H_2O$ (6:1, 5 ml) added. The mixture was stirred vigorously for 16 h and the resulting precipitate filtered, washed with 5% NaOH solution, water, dried ($MgSO_4$) and decanted. A solution of (+)-(4-methylthio-2-oxo-azetidin-1-yl)acetic acid (0.48 g, 2.8 mmol) in dichloromethane (5 ml) was added and the mixture stirred for 15 minutes and treated with a large excess of acetic acid. The reaction was washed carefully with saturated aq. $NaHCO_3$, dried ($MgSO_4$), evaporated and flash chromatographed ($Et_2O$/hexane 2:1) to give (+)-benzyl(4-methylthio-2-oxoazetidin-1-yl)acetate as a solid, 0.10 g, 13%, m.p.35–36° C.
Found: C, 58.6; H, 5.5; N, 5.4%; $C_{13}H_{15}NO_3S$ requires: C, 58.9; H, 5.7; N, 5.3%

EXAMPLE 30

(−)-Benzyl (4-methylthio-2-oxoazetidin-1-yl)acetate

Substituting (−)-(4-methylthio-2-oxo-azetidin-1-yl)acetic acid (0.48 g, 2.8 mmol) for (+)-(4-methylthio-2-oxo-azetidin-1-yl)acetic acid and using corresponding molar quantities of the other reagents in Example 29B gave (−)-benzyl (4-methylthio-2-oxo-azetidin-1-yl)acetate as a solid, 0.13 g, 18%, m.p.38–40° C.
Found: C, 58.5; H, 5.6; N, 5.3%; $C_{13}H_{15}NO_3S$ requires: C, 58.9; H, 5.7; N, 5.3%

EXAMPLE 31

(+)-Benzyl (4-methylsulphonyl-2-oxoazetidin-1-yl) acetate

Treatment of (+)-benzyl (4-methylthio-2-oxoazetidinyl-1-yl)acetate with mCPBA as described in Example 2 gave the title compound as colourless crystals, m.p.105–106° C., 38% yield Found: C, 52.5; H, 5.1; N, 4.7%; $C_{13}H_5NO_5S$ requires: C, 52.3; H, 5.1; N, 4.7%

EXAMPLE 32

(−)-Benzyl (4-methylsulphonyl-2-oxoazetidin-1-yl) acetate

Treatment of (−)-benzyl (4-methylthio-2-oxoazetidinyl-1-yl)acetate with mCPBA as described in Example 2 gave the title compound as colourless crystals, m.p.102–103° C., 87% yield Found: C, 52.5; H, 5.1; N, 4.7%; $C_{13}H_{15}NO_5S$ requires: C, 52.4; H, 4.9; N, 4.6%

EXAMPLE 33

6-(4-Fluorophenyl )hexyl (4-methylthio-2-oxoazetidin-1-yl)acetate

Substituting (4-methylthio-2-oxoazetidinyl)acetic acid for (3,3-dimethyl-4-methylthio-2-oxoazetidinyl)acetic acid in Example 48C gave the title compound as a colourless oil.

Found: C, 61.3; H, 6.9; N, 3.5%; $C_{18}H_{24}FNO_3S$ requires: C, 61.2; H, 6.8; N, 3.9%

EXAMPLE 34 trans-Benzyl (3-methyl-4-methylthio-2-oxoazetidin-1-yl)acetate

A. Trans-3-methyl-4-methylthioazetidin-2-one—Treatment of a mixture of cis and trans-3-methyl-4-acetoxyazetidin-2-one (RA Firestone et al., Tetrahedron, 1990, 46, 2255) with methane thiol under the conditions of Example 16A gave the title compound as a colourless oil after chromatography, 39% yield.

1H NMR δ (CDCl$_3$) 1.37 (3H, d, J=7.4 Hz, CH$_3$), 2.15 (3H,s,SCH$_3$), 3.17 (1H, dq, J=2.0, 7.4 Hz, H$_3$), 4.37 (1H, d, J=2.0 Hz, H$_4$), 6.67 (1H,brs,NH)

B. trans-Benzyl (3-methyl-4-methylthio-2-oxoazetidin-1-yl) acetate

Treatment of trans-3-methyl-4-methylthioazetidin-2-one with benzyl 1-bromoacetate under the conditions described in Example 16B gave trans-benzyl (3-methyl-4-methylthio-2-oxoazetidin-1-yl)acetate as a colourless oil, 25% yield Found: C, 60.1; H, 6.1; N, 5.2%; $C_{14}H_{17}NO_3S$ requires: C, 60.2; H, 6.1; N, 5.0%

Examples 35 and 36 were prepared by the method described for Examples 5 and 6.

EXAMPLE 35 trans-Benzyl (3-methyl-4-methylsulphinyl-2-oxoazetidin-1-yl)acetate colourless oil, 21%

$^1$H NMR (CDCl$_3$)δ:1.45, 1.45 (3H, 2×d, J=7.5 Hz, CH$_3$), 2.53, 2.58 (3H, 2×s, SOCH$_3$), 3.1, 3.8 (1H, 2×m, H$_3$), 3.82, 4.48, 4.15, 4.43, (2H, 2×d, J=18 Hz, N—CH$_2$), 4.4 (1H, m, H$_4$), 5.2 (2H, m, CH$_2$Ph), 7.38 (5H, m. Ph-H).

Found: C, 56.3; H, 5.8; N, 4.5%; $C_{14}H_{17}NO_4S.0.16\ H_2O$ requires:C, 56.4; H, 5.9; N, 4.7%

EXAMPLE 36 trans-Benzyl (3-methyl-4-methylsulphonyl-2-oxoazetidin-1-yl)acetate colourless oil, 56%

$^1$H NMR (CDCl$_3$)δ:1.46 (3H, d, J=7.4 Hz, CH$_3$), 2.92 (3H, s, SO$_2$CH$_3$), 3.5 (1H, m, 13), 4.0, 4.4 (each 1H, d, J=18.3 Hz, N—CH$_2$), 4.5 (1H, d, J=2.1 Hz, H$_4$), 5.19 (2H, s, CH$_2$Ph), 7.35 (5H, m, Ph-H).

Found: C, 53.5; H, 5.5; N, 4.2%; $C_{14}H_{17}NO_5S$ requires: C, 54.0; H, 5.5; N, 4.5%

EXAMPLE 37

4-Methylthio-1-(4-phenyl-3-oxoxbutyl )azetidin-2-one

A) 4-Bromo-1-phenylbutan-1-one—4-Bromobutyryl chloride (25 g, 0.135 mol) in dichloromethane (50 ml) was added dropwise over 5 minutes to a suspension of AlCl$_3$ in dichloromethane (100 ml) at room temperature. Stirring was continued at room temperature for 30 minutes, followed by addition of benzene (10.53 g, 0.135 mol) in dichloromethane (20 ml). The reaction mixture was stirred for 20 hours. The mixture was poured onto ice/water (200 g), ether (100 ml) was added and the organic layer was separated. This was washed with dil NaHCO$_3$, brine, and water until pH of solution was neutral. The combined organic layers were dried (MgSO$_4$), evaporated under reduced pressure to a brown oil (27.83 g). This was purified by flash chromatography on silica -el, using hexane/ether 15:1, 10:1, 1:1, then 1:2 to give the title compound as a solid (24.98 g, 81%).

B) 4-Iodo-1-phenylbutan-1-one—4-bromo-1-phenylbutan-1-one (22.71 g, 0.10 mol) was treated with NaI by the method described in Example 1 to give 4-iodo-1-phenylbutan-1-one (8.93 g, 92%).

C) 4-Iodo-1-phenylbutan-1-one ethylene acetal—A solution of 4-iodo-1-phenylbutan-1-one (8.53 g, 0.031 mol), ethylene glycol (3.85 g, 0.062 mol), and a catalytic amount of p—toluenesulfonic acid (0.29 g, 1.55 mmol) in dry benzene (250 ml) were azeotropically refluxed for 18 hours overnight using a Dean Stark apparatus. Then cooled and washed with dil NaHCO$_3$ and water, dried (MgSO$_4$), evaporated under reduced pressure to a yellow solid (10.45 g). This was purified by re crystallisation from ethyl acetate/petroleum ether 40° C.–60° C. to give yellow crystals (4.33 g). The mother liquor was evaporated to a solid and re crystallised from ethyl acetate/petroleum ether 40° C.–60° C. to give more yellow crystals (2.00 g, overall 64%).

D) 4-Methylthio-1-(4-phenyl-4-oxobutyl ethylene acetal) azetidin-2-one—Substituting 4-iodo-1-phenylbutan-1-one ethylene acetal (2.72 g, 8.53 mmol) for 1-bromo-4-phenylbutan-2-one and using corresponding molar quantities of the other reagents in Example 1 gave the title compound as a pale yellow solid (0.82 g, 31%).

E) 4-Methylthio-1-(4-phenyl-4-oxobutyl)azetidin-2-one—4-Methylthio-1-(4-phenyl-4-oxobutyl ethylene acetal) azetidin-2-one (0.75 g, 2.45 mmol) was dissolved in dry THF (30 ml) and ImI of 5% HCl was added everyday for 10 days with continuos monitoring by TLC. Then the THF was evaporated under reduced pressure to an oil and the oil was dissolved in ethyl acetate (50 ml), then washed with water, dil Na$_2$SO$_3$, dil NaHCO$_3$, and brine until pH of solution was neutral, dried (MgSO$_4$), evaporated to a solid (0.43 g). This was purified by recrystallisation from ether/petroleum ether 40° C.–60° C. to give the title compound as a pale yellow solid m.p. 57–60° C. (0.29 g, 44%).

1H NMR (CDCl$_3$) 2.07 (5H, m, CH$_2$CO+SCH$_3$), 2.94 (1H, dd, J=2, 15 Hz, H$_3$), 3.07 (2H, t, J=7.1 Hz, CH$_2$), 3.27 (1H, dd, J=5, 15 Hz, H$_3$), 3.15,3.4 (2H, 2×m, NCH$_2$), 4.7 (1H, m, H$_4$) 7.5, 7.9 (5H, 2×m, Ph-H)

EXAMPLE 38

4-Methylsulphinyl-1-(4-phenvl-4-oxobutyl)azetidin-2-one

Treatment of 4-methylthio-1-(4-phenyl-4-oxobutyl) azetidin-2-one (0.29 g, 1.09 mmol)with mCPBA as described in Example 2 gave the title compound as a yellow oil (0.27 g, 89%), $^1$H NMR (CDCl$_3$)δ:2.01–2.20 (4H, m, 2×CH$_2$CH$_2$CH$_2$), 2.49 (3H, s, SOCH$_3$), 2.61 (3H, s, SOCH$_3$), 2.79 (1H, dd, J=15.0, 2.25Hz, H$_{3a}$), 3.00–3.26 (6H, m, 2×CH$_2$CO, 2×H$_{3b}$), 3.42–4.07(5H, m, 2×N—CH$_2$, H$_{3a}$), 4.46(1H, m, H$_4$), 4.56(1H, m, H$_4$), 7.43–7.60, 7.93–7.97 (6H, 4H, m, Ar-H).

Found: C, 59.4; H, 6.2; N, 5.0%; C$_{14}$H$_{17}$NO$_3$S requires: C, 60.0; H, 6.2; N, 4.8%

EXAMPLE 39 cis-Benzyl (3-methyl-4-methylthio-2-oxoazetidin-1-yl)acetate

A. Cis-3-methyl-4-methylthioazetidin-2-one—Treatment of a mixture of cis- and trans-3-methyl-4-acetoxyazetidin-2-one (RA Firestone et al., Tetrahedron, 1990, 46, 2255) with methyl thiol under the conditions of Example 16A gave the title compound as a colourless oil after chromatography, 5% yield $^1$H NMR 8 (CDCl$_3$) 1.33 (3H, d, J=7.6 Hz, CH$_3$), 2.16 (3H, s, SCH$_3$), 3.55 (1H, m, H$_3$), 4.78 (1H, d, J=5 Hz, H$_4$), 6.22 (1H,brs,NH)

B. Cis-Benzyl (3-methyl-4-methylthio-2-oxoazetidin-1-yl) acetate

Treatment of cis-3-methyl-4-methylthioazetidin-2-one with benzyl 1-bromoacetate under the conditions described in Example 16B gave cis-benzyl (3-methyl-4-methylthio-2-oxoazetidin-1-yl)acetate as acolourless oil, 40% yield $^1$H NMR (CDCl$_3$)δ:1.29 (3H, d, J=7.6 Hz, CH$_3$), 2.08 (3H, s, SCH$_3$), 3.61 (1H, m, H$_3$), 3.78, 4.38 (each 1H, d, J=18.0 Hz, N—CH$_2$), 4.94 (1H, d, J=4.9hz, H$_4$), 5.18 (2H, s, CH$_2$Ph), 7.36 (5H, m, Ph-H)

Found: C, 60.2; H, 6.1; N, 4.9%; C$_{14}$H$_{17}$NO$_3$S requires: C, 60.2; H, 6.1; N, 5.0%

Examples 40 and 41 were prepared by the method described for Examples 5 and 6.

EXAMPLE 40 cis-Benzyl (3-methyl-4-methylsulphinyl-3-oxoazetidin-1-yl)acetate colourless oil, 42%

$^1$H NMR (CDCl$_3$)δ:1.34 (3H, d, J=7.7 Hz, CH$_3$), 2.59 (3H, s, SOCH$_3$), 3.66 (1H, m, H$_3$), 4.23,4.45 (each 1H, d, J=18.3 Hz, N—CH$_2$), 4.67 (1H, d, J=5.1 Hz, H$_4$), 5.18 (2H, s, CH$_2$Ph), 7.36 (5H, m, Ph-H)

Found: C, 56.4; H, 5.8; N, 4.3%; C$_{14}$H$_{17}$NO$_4$S requires: C, 56.9; H, 5.8; N, 4.7%

EXAMPLE 41 cis Benzyl (3-methyl-4-methylthio-2-oxoazetidin-1-yl)acetate colourless oil, 48%

$^1$H NMR 8 (CDCl$_3$) 1.53 (3H, d, J=7.7 Hz, CH$_3$), 2.92 (3H, s, SO$_2$CH$_3$), 3.82 (1H, m, H$_3$), 3.92, 4.49 (each 1H, d, J=18.3 Hz, N—CH$_2$), 4.93 (1H, d, J=5.4 Hz, H$_4$), 5.18 (2H, s, CH$_2$Ph), 7.36 (5H, m, Ph-H)

Found: C, 53.8; H, 5.6; N, 4.2%; C$_{14}$H$_{17}$NO$_5$S +1.1% w/w EtOAc requires: C, 54.0; H, 5.5; N, 4.5%

EXAMPLE 42 trans-Benzyl (3,3-dimethyl-4-methylthio-2-oxoazetidin-1-yl)acetate

A. 3,3-dimethyl-4-methylthioazetidin-2-one—Treatment of 3,3-dimethyl-4-acetoxyazetidin-2-one (RA Firestone et al., Tetrahedron, 1990, 46, 2255) with methyl thiol under the conditions of Example 16A gave the title compound $^1$H NMR 8 (CDCl$_3$)

B. Benzyl (3,3-dimethyl-4-methylthio-2-oxoazetidin-1-yl) acetate

Treatment of 3,3-dimethyl-4-methylthioazetidin-2-one with benzyl 1-bromoacetate under the conditions described in Example 16B gave cis-benzyl (3-methyl-4-methylthio-2-oxoazetidin-1-yl)acetate as a pale yellow oil, 31% yield Found: C, 61.3; H, 6.4; N, 4.4%; C$_{15}$H$_{19}$NO$_3$S requires: C, 61.4; H, 6.5; N, 4.8%

Examples 43 and 44 were prepared by the method described for Examples 2 and 3.

EXAMPLE 43

Benzyl (3,3-dimethyl-4-methylsulphonyl-2-oxoazetidin-1-yl)acetate colourless oil, 49% yield Found: C,55.2; H, 5.8; N, 4.0%; C$_{15}$H$_{19}$NO$_5$S requires: C, 55.4; H,5.9; N, 4.3%

EXAMPLE 44

Benzyl (3,3-dimethyl-4-methylsulphinyl-2-oxoazetidin-1-yl)acetate Colourless oil, 50% yield Found: C, 58.0; H, 6.2; N, 4.7%; C$_{15}$H$_{19}$NO$_4$S requires: C, 58.2; H, 6.2; N, 4.5%

EXAMPLE 45

Benzyl (3,3-diethyl-4-methylthio-2-oxoazetidin-1-yl)acetate

A. 3,3-diethyl4-methylthioazetidin-2-one—Substituting 3,3-diethyl-4-acetoxyazetidin-2-one (SK Shah et al, J Med Chem, 1992, 35, 3745) (10 g, 0.053 mol) for 4-acetoxyazetidinone and excess methanethiol and using corresponding molar quantities of the other reagents in Example 16A gave 3,3-diethyl-4-methylthioazetidin-2-one 5.9 g, 65% as an oil.

$^1$H NMR (CDCl$_3$)δ:0.82–1.07 (6H, m, 2×CH$_2$CH$_3$), 1.64–1.90 (4H, m, 2×CH$_2$CH$_3$), 2.17 (3H, s, SCH$_3$), 4.43 (1H, s, H$_4$), 6.87 (1H, bs, NH).

B. Benzyl (3,3-diethyl-4-methylthio-2-oxoazetidin-1-yl) acetate

Treatment of 3,3-diethyl-4-methylthioazetidin-2-one with benzyl 1-bromoacetate under the conditions described in Example 16B gave benzyl (3,3-diethyl-4-methylthio-2-oxoazetidin-1-yl)acetate as colourless oil.

$^1$H NMR 8 (CDCl$_3$) 1.02 (6H, m, 2×CH$_2$CH$_3$), 1.72 (4H, m, 2×CH$_2$CH$_3$), 2.08 (3H, s, SCH$_3$), 3.81 and 4.38 (each 1H, d, J=18 Hz, N—CH$_2$), 4.59 (1H, s, H$_4$), 5.12 and 5.23 (each 1H, d, J=12 Hz, OCH$_2$Ph), 7.36 (bs, 5H, Ph-H)

Examples 46 and 47 were prepared by the method described for Examples 2 and 3.

EXAMPLE 46

Benzyl (3,3-diethyl-4-methylsulphinyl-2-oxoazetidin-1-yl)acetate

Colouriess crystals, m.p. 98° C., 70% yield

Found: C, 60.2; H, 6.6; N, 4.2%; C$_{17}$H$_{23}$NO$_4$S requires: C, 60.5; H, 6.9; N, 4.2%

EXAMPLE 47

Benzyl (3,3-diethyl-4-methylsulphonyl-2-oxoazetidin-1-yl)acetate colourless crystals m.p. 99° C., 88% yield Found: C, 57.2; H, 6.4; N, 3.9%; C$_{17}$H$_{23}$NO$_5$S 0.2 H$_2$O requires: C, 57.2; H, 6.4; N, 3.9%

EXAMPLE 48

4-Fluorophenylhexyl(3,3-diethyl-4-methylthio-2-oxoazetidin-1-yl)acetate

A. Methyl(3,3-diethyl-4-methylthio-2-oxo-azetidin-1-yl) acetate To a solution of 3,3-diethyl-4-methylthioazetidin-2-one (1.2 g, 6.9 mmol) in dry THF (50 ml) at −78° C. was added dropwise a 1 molar solution of lithuim hexamethyldisilazide in dry THF (6.9 ml, 6.9 mmol). Stirring was continued for 1 hr and methyl bromoacetate (2.6 g, 16.7 mmol) was added dropwise and the resulting mixture stirred at −78° C. for 30 mins. The temperature was allowed to warm to 0° C. and EtOAc (50 ml) added. The solution was washed with brine, separated, dried ($Na_2SO_3$), filtered and evaporated. The residue was purified by flash chromatography (hexane/ethyl acetate 10–20%) to give methyl (3,3-diethyl-4-methylthio-2-oxo-azetidin-1-yl)acetate, 0.82 g, 49% as an oil.

$^1$H NMR ($CDCl_3$)δ:0.95–1.05 (6H, m, 2×$CH_2CH_3$), 1.60–1.89 (4H, m, 2×$CH_2CH_3$), 2.14 (3H, s, $SCH_3$), 3.74 (3H, s, $OCH_3$), 3.7, 4.27 (each 1H, d, J=17.5 Hz, N—$CH_2$), 4.62 (1H, s, $H_4$).

B. 4-Fluorophenylhexyl(3,3-diethyl-4-methylthio-2-oxoazetidin-1-yl)acetate-Methyl (3,3-diethyl-4-methylthio-2-oxo-azetidin-1-yl)acetate (0.8 g, 3.2 mmol) was dissolved in benzene with 4-fluorophenylhexylalcohol (1.3 g, 6.5 mmol) and sodium methoxide (SOmg ,0.9 mmol) and the mixture refuxed for 2 h. The reaction mixture was evaporated and diluted with EtOAc, the solution washed with water, separated, dried ($K_2CO_3$) and flash chromatographed (hexane/ethyl acetate 9:1) to give 4-fluorophenylhexyl(3,3-diethyl-4-methylthio-2-oxoazetidin-1-yl)acetamide 0.17 g, 14% as an oil.

Found: C, 64.20; H, 7.75; N, 3.23%; $C_{22}H_{32}FNO_3S$ requires: C, 64.52: H, 7.88; N, 3.42%

EXAMPLE 49

N-Benzyloxy-(4-methyl thio-2-oxo-azetidin-1-yl)acetamide

Triethylamine (2 ml) was added to a solution of (4-methylthio-2-oxo-azetidin-1-yl)acetic acid (1.67 g) in dry chloroform (15 ml) cooled to −10° C. After 5 mins ethyl chloroformate (1.6 ml) was added, then after a further 5 mins a solution of O-benzylhydroxylamine free base (1.67 g) in chloroform was added. The solution was allowed to warm to room temperature and stirred for 16 hours then washed with brine, dried ($MgSO_4$) and evaporated. Chromatography of the residue on silica gel (petroleun ether/ethyl acetate) gave N-benzyloxy-(4-methylthio-2-oxo-azetidin-1-yl)acetamide as a clear gum (22% yield).

Found: C, 55.3; H, 5.3; N, 10.0%; $C_{13}H_{16}N_2O_3S$ requires: C, 55.7, H, 5.7; N, 10.0%

Examples 50 and 52 were prepared by the same method as Example 49. Examples 51, 53 and 54 were prepared from Examples 50 and 52 by the same method as described for Examples 2 and 3.

EXAMPLE 50

N-(2-Phenylethyloxy)-(4-methylthio-2-oxo-azetidin-1-yl)acetamide

Cream solid, m.p. 74–76° C., 34% yield
Found: C, 57.3; H, 6.1; N, 9.4%; $C_{14}H_{18}N_2O_3S$ requires: C, 57.1, H, 6.2; N, 9.5%

EXAMPLE 51

N-(2-Phenylethyloxy)-(4-methylsulfinyl-2-oxo-azetidin-1-yl)acetamide Granular gum, 60:40 mixture of diastereoisomers (not assigned), 64% yield $^1$H NMR δ (DMSO-$d_6$) 2.56 and 2.46 (3H, s, $SCH_3$ and $SCH_3$), 2.88 (3H, t, J=7 Hz, $CH_2Ph$), 3.03 (1H, dd, J=2, 15 Hz, $H_{3a}$), 3.19 (1H, dd, J=5, 15 Hz, $H_{3b}$), 3.25 (1H, d, J=3 Hz, $H_{3a'}$), 3.31 (1H, d, J=18 Hz, $H_{3b'}$), 3.66 and 3.86 (each 1H, d, J=17 Hz, N—$CH_2$), 3.95–4.09 (>2H, m, $OCH_2$, N'-$CH_2$), 4.75 (<1H, m, $H_{4'}$), 4.80 (1H, m, $H_4$), 7.29–7.17 (5H, m, Ph-H), 11.34 (1H, bs, NH)

EXAMPLE 52

N-(2-Phenylpropyloxy)-(4-methylthio-2-oxo-azetidin-1-yl)acetamide Colourless gum, 57% yield Found: C, 56.6; H, 6.3; N, 8.4%; $C_{15}H_{20}N_2O_3S$ 0.55 $H_2O$ requires: C, 56.6, H, 6.7; N, 8.8%

EXAMPLE 53

N-(2-Phenylpropyloxy)-(4-methylsulfinyl-2-oxo-azetidin-1-yl)acetamide White wax, 57% yield $^1$H NMR δ (DMSO-$d_6$) 1.85 (2H, m, $CH_2CH_2CH_2Ph$), 2.66 (2H, t, J=7.5 Hz, $CH_2Ph$), 3.13 (3H, s, $SO_2CH_3$), 3.28 (1H, dd, J=<2, 15.5 Hz, $H_{3a}$), 3.47 (1H, dd, J=5,15.5 Hz, $H_{3b}$), 3.77 (2H, t, J=6 Hz, $OCH_2$), 4.04 and 3.73 (each 1H, d, J=17 Hz, N—$CH_2$), 4.96 (1H, m, $H_4$), 7.16–1.30 (5H, m, Ph-H), 11.25 (1H, bs, NH)

EXAMPLE 54

N-(2-Phenylpropyloxy)-(4-methylsulfonyl-2-oxo-azetidin-1-yl)acetamide Cream wax, 54% yield Found: C, 56.6; H, 6.3; N, 8.4%; $C_{15}H_{20}N_2O_5S$ 0.55 $H_2O$ requires: C, 56.6, H, 6.7; N, 8.8%

EXAMPLE 55

(±)-N-Benzyl-(4-methylthio-2-oxoazetidin-1-yl)acetamide

A solution of benzylamine (0.58 g, 5.4 mmol), dicyclohexylcarbodiimide (DCC) (1.13 g, 5.5 mmol), hydroxybenzotriazole (HOBT) (0.74 g, 5.5 mmol) and (±)-(4-methylthio-2-oxoazetidin-1-yl)acetic acid (1.04 g, 5.9 mmol) in DMF (15 ml) was stirred at room temperature for 2 hours. Ethyl acetate (40 ml) was added and the reaction mixture filtered, the filtrate washed with dil $NaHCO_3$, water (×2) and dried ($MgSO_4$) and evaporated to an oil (1.02 g). The oil was crystallised from ether/ethyl acetate to give a white solid (0.90 g) which was purified by flash chromatography on silica gel using petroleum ether/ethyl acetate to give N-benzyl-(4-methylthio-2-oxoazetidin-1-yl)acetamide as a colourless solid (0.66 g, 46%), m.p. 84–87° C.

$^1$H NMR ($CDCl_3$)δ:2.03 (3H, s, $SCH_3$), 2.96 (1H, dd, J=15.25, 2.25Hz, $H_{3a}$), 3.37 (1H, dd, J=15.25, 5.00 Hz, $H_{3b}$), 3.57, 4.02 (each 1H, d, J=16.75 Hz, N—$CH_2$), 4.45 (2H, t, J=4.25 Hz, $CH_2Ph$), 4.82 (1H, m, $H_4$), 6.62 (1H, s, CONH), 7.17–7.37 (5H, m, Ph-H).

Found: C, 59.4; H, 6.4; N, 10.5%; $C_{13}H_{16}N_2O_2S$ requires: C, 59.1; H, 6.1; N, 10.6%

EXAMPLE 56

(±)-N-Benzyl-(4-methylsuphinyl-2-oxoazetidin-1-yl)acetamide

Substituting N-benzyl-(4-methylthio-2-oxoazetidin-1-yl)acetamide (0.60 g, 2.27 mmol) for 4-methylthio-1-(4- phenyl-2-oxobutyl)azetidin-2-one and using corresponding molar quantities of the other reagents in Example 2 gave (±)-N-benzyl-(4-methylsuphinyl-2-oxoazetidin-1-yl) acetamide as a yellow/green oil.

$^1$H NMR (CDCl$_3$)δ:2.45 (3H, s, SOCH$_3$), 2.59 (3H, s, SOCH$_3$), 2.99 (1H, dd, J=15.0, 2.0 Hz, H$_{3a}$), 3.22 (1H, dd, J=15.0, 5.0 Hz, H$_{3b}$), 3.31 (1H, dd, J=15.0, 5.5 Hz, H$_{3b}$), 3.34 (1H, dd, J=15.0, 2.5 Hz, H$_{3a}$), 3.75, 4.14 (each 1H, d, J=17.0 Hz, N—CH$_2$), 3.94, 4.17 (2H, dd, J=17.0 Hz, N—CH$_2$), 4.30 (4H, m, 2×Cl$_2$Ph), 4.79 (1H, m, H$_4$), 4.84 (1H, m, 14), 7.22–7.34 (10H, m, 2×Ph-H), 8.59 (1H, m, NH), 8.70 (1H, m, NH).

EXAMPLE 57

N-Benzyl-(4-methylsuphonyl-2-oxoazetidin-1-yl) acetamide

A solution of mCPBA (0.49 g, 1.42 mmol) in dry dichloromethane (40 ml) was added dropwise over 10 minutes to a solution of N-benzyl-(4-methylthio-2-oxoazetidin-1-yl) acetamide in dry dichloromethane (30 ml) at room temperature and stirred for 2.5 hours. After 2 hours a further aliquot (0.1 g) of mCPBA was added. The solution was washed with dil Na$_2$SO$_3$, dil NaHCO$_3$ and H$_2$O, dried (MgSO$_4$) and evaporated under reduced pressure to an oil (0.28 g). This oil was purified by flash chromatography on silica gel (ethyl acetate/ethanol) to give N-benzyl-(4-methylsuphonyl-2-oxoazetidin-1-yl)acetamide as a colourless solid, (0.08 g, 24%).

$^1$HNMR (CDCl$_3$)δ:2.94 (3H, s, SO$_2$CH$_3$), 3.31 (1H, dd, J=15.20,2.4 Hz, H$_{3a}$), 3.46 (1H, dd, J=15.20, 5.20 Hz, H$_{3b}$), 4.00, 4.17 (each 1H, d, J=16.8 Hz, N—CH$_2$), 5 4.46 (2H ,d, J=5.6 Hz, CH$_2$Ph), 4.92 (1H, m, H$_4$), 6.15 (1H, m, CONH), 7.26–7.37 (5H, m, Ph-H).

Found: C, 52.3; H, 5.4; N, 9.6%; C$_{13}$H$_{16}$N$_2$O$_4$S requires: C, 52.7; H, 5.4; N, 9.5%

EXAMPLE 58

R$^c$,R$^s$-(−)-N-Benzyl-(4-methylsulphiny-2-oxoazetidin-1-yl)acetamide

A. 4R-(+)-N-Benzyl-(4-methylthio-2-oxoazetidin-1-yl) acetamide Substituting (−)-(4-methylthio-2-oxo-azetidin-1-yl)acetic acid (0.35 g, 1.99 mmol) for (±)-(4-methylthio-2-oxoazetidin-1-yl)acetic acid and using corresponding molar proportions of the other reagents in Example 55 gave 4R-(+)-N-benzyl-(4-methylthio-2-oxoazetidin-1-yl)acetamide as an oil 0.19 g, 40%.

$^1$H NMR (CDCl$_3$)δ:2.03 (3H, s, SCH$_3$), 2.95 (1H, dd, J=15, 5Hz, H$_{3a}$), 3.41(1H, dd, J=15, 2.2 Hz, H$_{3b}$), 3.78, 3.99 (each 1H, dd, J=17 Hz, N—CH$_2$), 4.45 (2H, m, PhCH$_2$), 4.83 (1H, m, H$_4$), 6.60 (1H, bs, NH), 7.28 (5H, m, Ph-H)

B. 4RSR-(−)-N-Benzyl-(4-methylsulphinyl-2-oxoazetidin-1-yl )acetamide A solution of S(−)1,1'-bi-2-napthol (0.012 g, 4.2 μmol) in toluene (2 ml) was treated with titanium isopropoxide (0.012 g, 21 μmol) in water (6 mg, 0.033 mmol). The resulting mixture was stirred at room temperature for 1 h. A solution of (−)-N-Benzyl (4-methylthio-2-oxoazetidin-1-yl)acetamide (0.2 g, 0.76 mmol) in toluene was added. After 30 mins t-butylhydroperoxide (136 mg, 1.5 mmol) was added and the mixture stirred for 3h. After evaporation to dryness, the residue was purified by flash chromatography on silica (EtOAc/EtOH 6:1 to 3:1) to give (−)-N-benzyl-(4-methylthio-2-oxoazetidin-1-yl)acetamide as a solid, 70 mg, 33% m.p. 138–140° C, [α]$_D^{25}$=−237° (c=1.35, EtOH).

Found: C, 55.9; H, 5.7; N, 9.8%; C$_{13}$H$_{16}$N$_2$O$_3$S requires: C, 55.7; H, 5.8; N,10.0%

EXAMPLE 59

4R,SS-(+)-N-Benzyl-(4-methylsulphinyl-2-oxoazetidin-1-yl)acetamide

Substituting 4R-(+)-N-benzyl-(4-methylthio-2-oxoazetidin-1-yl)acetamide (0.18 g, 0.72 mmol) for 4-methylthio-1-(4-phenyl-2-oxobutyl)azetidin-2-one and using corresponding molar quantities of the other reagents in Example 2 gave a mixture of 4R,SR-(−)-N-benzyl-(4-methylsulphinyl-2-oxoazetidin-1-yl)acetamide and R$^c$,S$^s$-(+)-N-benzyl-(4-methylsulphinyl-2-oxoazetidin-1-yl) acetamide which were separated by preparative HPLC (Beckmann silica column isocratically eluted with hexane:EtOH 45:55). Evaporation of the appropriate fractions gave 4R,SS-(+)-N-benzyl-(4-methylsulphinyl-2-oxoazetidin-1-yl)acetamide, 0.01 g, 6.2%, m.p. **° C.

$^1$H NMR (CDCl$_3$)δ:2.48 (3H, s, SOCH3), 3.05 (1H, dd, J=15, 5 Hz, H$_{3a}$), 3.35 (1H, dd, J=15, 2.2 Hz, H$_{3b}$), 3.95, 4.25 (each 1H, d, J=17 Hz, N—CH$_2$), 4.45 (2H, m, PhCH$_2$), 4.60 (1H, m, H$_4$), 7.30 (SH, m, Ph-H), 7.60 (1H, bs, NH),.

EXAMPLE 60

4S,SS-(+)-N-Benzyl-(4-methylsulphinyl-2-oxoazetidin-1-yl)acetamide

A. 4S-(−)-N-Benzyl-(4-methylthio-2-oxoazetidin-1-yl) acetamide—Substituting (+)-(4-methylthio-2-oxo-azetidin-1-yl)acetic acid (0.33 g, 1.99 mmol) for (±)-(4-methylthio-2-oxoazetidin-1-yl)acetic acid and using corresponding molar proportions of the other reagents in Example 55 gave 4S-(−)-N-benzyl-(4-methylthio-2-oxoazetidin-1-yl)acetamide as an oil 0.25 g, 53%.

$^1$H NMR (CDCl$_3$)δ:2.04 (3H, s, SCH$_3$), 3.01 (1H, dd, J=15, 5 Hz, H$_{3a}$), 3.37 (1H, dd, J=15,2.2 Hz, H$_{3b}$), 3.83, 4.01(each 1H, d, J=17 Hz, N—CH$_2$), 4.46 (2H, m, PhCH$_2$), 4.83 (1H, m, H$_4$), 6.60 (1H, bs, NH), 7.28 (5H, m, Ph-H)

B. 4SSS-(+)-N-Benzyl-(4-methylsulphinyl-2-oxoazetidin-1-yl)acetamide—Substituting 4S-(−)-N-benzyl-(4-methylthio-2-oxoazetidin-1-yl)acetamide (0.23 g, 0.91 mmol) for 4-methylthio-1-(4-phenyl-2-oxobutyl)azetidin-2-one and using corresponding molar quantities of the other reagents in Example 2 gave a mixture of 4S,SS-(+)-N-benzyl-(4-methylsulphinyl-2-oxoazetidin-1-yl) acetamide and 4S,SR-(−)-N-benzyl-(4-methylsulphinyl-2-oxoazetidin-1-yl)acetamide which were separated by preparative HPLC (Beckmann silica column isocratically eluted with hexane:EtOH 45:55). Evaporation of the appropriate fractions gave 4S,SS-(+)-N-benzyl-(4-methylsulphinyl-2-oxoazetidin-1-yl)acetamide, 0.017 g, 7%, as a colourless oil, [α]$_D^{25}$=+220°.

Found: C, 55.4; H, 5.6; N, 9.3%; C$_{13}$H$_{1-6}$N20$_3$S 0.2 EtOH requires: C, 55.6; H, 6.0; N, 9.7%

EXAMPLE 61

4S,SR-(−)-N-Benzyl-(4-methylsulphinyl-2-oxoazetidin-1-yl)acetamide

This was obtained by evaporation of the appropriate fractions in Example 60B and was obtained as a colourless oil, 4mg, 1.5%

$^1$H NMR (CDCl$_3$)δ:2.49 (3H, s, SOCH$_3$), 3.09 (1H, m, H$_3$), 3.40 (1H, m, H$_3$), 3.95, 4.28 (each 1H, d, J=17Hz, N—CH$_2$), 4.45 (2H, m, PhCH$_2$), 4.62 (1H, m, H$_4$), 7.25–7.35 (5H, M, Ph-H), 7.55 (1H, b, NH).

Examples 62 to 79 were prepared by methods analogous to those used for Examples 55 to 57.

EXAMPLE 62

N-6-Phenylhexyl-(4-methylthio-2-oxoazetidin-1-yl) acetamide

Yellow oil, 80% yield $^1$H NMR (CDCl$_3$)δ:1.30 (4H, m, CH$_2$CH$_2$), 1.45–1.67 (4H, m, NHCH$_2$CH$_2$, CH$_2$CH$_2$Ph), 2.09 (3H, s, SCH$_3$), 2.59 (2H, t, J=7.50 Hz, CH$_2$Ph), 2.99 (1H, dd, J=15.25, 2.25 Hz, H$_{3a}$), 3.29 (2H, m, NHCH$_2$), 3.41 (1H, dd, J=15.25, 5.00 Hz, H$_{3b}$) 3.76, 3.96 (each 1H, d, J=16.75 Hz, N—CH$_2$), 4.82 (1H, m, H$_4$), 6.22 (1H, s, CONH), 7.14–7.30 (5H, m, Ph-H).

Found: C, 64.3; H, 7.8; N, 8.1%; C$_{18}$H$_{26}$N$_2$O$_2$S requires: C, 64.6; H, 7.8; N, 8.4%

EXAMPLE 63

N-6-Phenylbexyl-(4-methylsulphinyl-2-oxoazetidin-1-yl)acetamide

Waxy yellow solid, 78% yield $^1$H NMR (CDCl$_3$) 6: 1.25–1.72 (16H, m, 2×CH$_2$CH$_2$CH$_2$CH$_2$), 2.50 (3H, s, SOCH$_3$), 2.60 (4H, t, J=8.0 Hz, 2×CH$_2$Ph), 2.61 (3H, s, SOCH$_3$), 3.11 (1H, dd, J=15.25, 2.25 Hz, H$_{3a}$), 3.14–3.38 (5H, m, 2×NHCH$_2$, H$_{3b}$), 3.39 (1H, dd, J=15.25, 5.25 Hz, H$_{3b}$), 3.60 (lH, dd, J=14.75, 2.25 Hz, H$_{3a}$), 3.84, 4.14 (each 2H, 2×d, J=17.25,17.25 Hz, N—CH$_2$), 4.61(1H, m, H$_4$), 4.65 (1H, m, H$_4$), 6.69 (2H, s, 2×CONH), 7.13–7.30 (10H, m, Ph-H).

EXAMPLE 64

N-6-Phenylhexyl-(4-methylsulphonyl-2-oxoazetidin-1-yl)acetamide

Colourless solid, m.p. 86–88° C., 80% yield

Found: C, 59.0; H, 6.8; N, 7.9%; C$_{18}$H$_{26}$N$_2$O$_4$S requires: C, 59.0; H, 7.1; N, 7.6%

EXAMPLE 65 trans-N-Benzyl-(3-methyl-4-methylthio-2-oxoazetidin-1-yl)acetamide

Colourless oil, 61% yield $^1$H NMR (CDCl$_3$)δ:1.37 (3H, d, J=7.4 Hz, CH$_3$), 2.04 (3H, s, SCH$_3$), 3.19 (1H, m, H$_3$), 3.81, 4.00 (each 1H, d, J=16.6 Hz, N—CH$_2$), 4.44 (3H, m, CH$_2$Ph, H$_4$), 6.52 (1H, br s, NH), 7.3 (5H, m, Ph-H)

EXAMPLE 66 trans-N-Benzyl-(3-methyl-4-methylsulphinyl-2-oxoazetidin-1-yl)acetamide colourless oil, 19% yield $^1$H NMR (CDCl$_3$)δ:1.45,1.48 (3H, 2×d, J=7.6 Hz, CH$_3$), 2.47, 2.53 (3H, 2×s, SOCH3), 3.29, 3.86 (1H, 2×m, H$_3$), 3.9–4.5 (5H, m, N—CH$_2$, CH$_2$Ph, H$_4$) 7.0, 7.5 (1H, 2×br s, NH), 7.3 (5H, m, Ph-H)

EXAMPLE 67 trans-N-benzyl-(3-methyl-4-methylsulphonyl-2-oxoazetidin-1-yl)acetamide colourless oil, 42% yield Found: C, 53.9; H, 5.8; N, 9.2%; C$_{14}$H$_{18}$N$_2$O$_4$S requires: C, 54.2; H, 5.9; N, 9.0%

EXAMPLE 68 cis-N-(6-Phenylhexyl)-(3-methyl-4-methylthio-2-oxoazetidin-1-yl)acetamide

Colourless oil, 46% yield $^1$H NMR (CDCl$_3$)δ:1.2–1.7 (8H, m, 4×CH$_2$), 1.31 (3H, d, J=7.6 Hz, CH$_3$), 2.20 (3H, s, SCH$_3$), 2.60 (2H, t, J=7.6 Hz, CH$_2$Ph), 3.25 (2H, m, NHCH$_2$), 3.60 (1H, m, 13), 3.89 (2H, s, NCH$_2$), 4.87 (1H, d, J=5.1 Hz, H$_4$), 6.24 (1H, br s, NH), 7.2–7.3 (5H, m, Ph-H)

Found: C, 64.9; H, 7.8; N, 7.6; S, 9.0%; C$_{19}$H$_{28}$N$_2$O$_2$S requires: C, 65.5; H, 8.1; N, 8.0; S, 9.2%

EXAMPLE 69 cis-N-(6-Phenylhexyl)-(3-methyl-4-methylsulfinyl-2-oxoazetidin-1-yl)acetamide colourless waxy solid Found: C, 62.56; H, 7.70; N, 7.54; C$_{19}$H$_{28}$N$_2$O$_3$S requires: C, 62.61; H, 7.74; N, 7.69%

EXAMPLE 70 trans-N-(6-Phenylhexyl)-3-(methyl-4-methylthio-2-oxoazetidin-1-yl)acetamide colourless oil, 59% yield Found: C, 65.2; H, 8.0; N, 7.8%; C$_{19}$H$_{28}$N$_2$O$_2$S requires: C, 65.5; H, 8.1; N, 8.0%

EXAMPLE 71 trans-N-(6-phenylhexyl)-(3-methyl-4-methylsulphinyl-2-oxoazetidin-1-yl)acetamide colourless oil, 75% yield $^1$H NMR (CDCl$_3$)δ:1.2–1.75 (11H, m, CH$_3$,4×CH$_2$), 2.56 (5H, m, SOCH$_3$, CH$_2$Ph), 3.24 (2H, m, NHCH$_2$), 3.33 (1H, m, H$_3$), 3.8–4.3 (2H, m, NCH$_2$), 4.27 (1H, m, H$_4$), 6.67 (1H ,br s, NH), 7.13–7.30 (5H, m, Ph-H)

EXAMPLE 72 trans N-(6-Phenylhexyl)-(3-methyl-4-methylsulphonyl-2-oxoazetidin-1-yl)acetamide colourless solid, m.p. 91–2° C., 74% yield Found: C, 60.0; H, 7.3; N, 7.5%; C$_{19}$H$_{28}$N$_2$O$_4$S requires: C, 60.0; H, 7.3; N, 7.5%

EXAMPLE 73

N-Benzyl-(3,3-dimethyl-4-methylthio-2-oxoazetidin-1-yl)acetamide colourless solid, m.p. 59–62° C., 79% yield Found: C, 61.7; H, 6.8; N, 9.9%; C$_{15}$H$_{20}$N$_2$O$_2$S requires: C, 61.6; H, 6.9; N, 9.6%

EXAMPLE 74

N-Benzyl-(3,3-dimethyl-4-methylsulphinyl-2-oxoazetidin-1-yl)acetamide, (94% diastereoisomer 2)

colourless oil, 43% yield
Found: C, 50.7; H, 5.6; N, 7.5%; $C_{15}H_{20}N_2O_3S \cdot 0.8CH_2Cl_2$ requires: C, 50.4; H, 5.8; N, 7.4%

EXAMPLE 75

N-Benzyl-(3,3-dimethyl-4-methylsulphinyl-2-oxoazetidin-1-yl)acetamide, (>99% diastereoisomer 1)

colourless oil, 16% yield
Found: C, 53.0, H, 6.1; N, 8.6%; $C_{15}H_{20}N_2O_3S \cdot 0.5CH_2Cl_2$ requires: C, 53.1; H, 6.0; N, 8.0%

EXAMPLE 76

N-Benzyl-(3,3-dimethyl-4-methylsulphonyl-2-oxoazetidin-1-yl)acetamide Colourless oil, 76% yield Found: C, 55.3; H, 6.3; N, 8.6%; $C_{15}H_{20}N_2O_4S$ requires: C, 55.5; H, 6.2; N, 8.6%

EXAMPLE 77

N-(6-Phenylhexyl)-(4-n-hexylthio-2-oxoazetidin-1-yl)acetamide

Yellow oil
$^1$H NMR (CDCl$_3$)δ:0.89 (3H, t, J=6.7 Hz, CH$_3$), 1.3 (10H, m, 5×CH$_2$), 1.59 (6H, m, 3×CH$_2$), 2.58 (4H, m, PhCH$_2$, SCH$_2$), 2.94, 3.01 (1H, dd, J=2.4, 15.3 Hz, H$_{3a}$), 3.45 (2H, m, CONHCH$_2$), 3.41, 3.48 (1H, dd, J=5.1, 15.3 Hz, H$_{3b}$?), 3.79, 3.94 (each 1H, d, J=20.7 Hz, N—CH$_2$), 4.84 (1H, m, H$_4$), 6.2 (1H, m, NH), 7.2 (5H, m, Ph-H)

EXAMPLE 78

N-(6-Phenylhexyl)-(4-n-hexylsulfinyl-2-oxoazetidin-1-yl)acetamide, (>99% diastereoisomer 1)

Colourless crystalline solid, m.p. 118–119° C.
Found: C, 65.5; H, 8.3; N, 6.9%; C23H36N2O3S requires: C, 65.7; H, 8.6; N, 6.7%

EXAMPLE 79

N-(6-Phenylhexyl)-(4-n-hexylsulfinyl-2-oxoazetidin-1-yl)acetamide, (96% diastereoisomer 2)

Colourless solid, m.p. 70–71° C.
Found: C, 65.3; H, 8.3; N, 6.7%; $C_{23}H_{36}N_2O_3S$ requires: C, 65.7; H, 8.6; N, 6.7%

EXAMPLE 80

4-Methylthio-1-benzyl-azetidin-2-one

A solution of 4-methylthioazetidin-2-one (1.0 g, 8.53 mmol) in dry THF (10 ml) was added dropwise to a suspension of NaH (0.35 g, 8.63 mmol) in dry THF (5 ml) at −20° C. under an inert atmosphere. Benzyl bromide (1.46 g, 8.53 mmol) in dry THF (10 ml) was added dropwise over 15 minutes at −55° C. The resultant mixture was stirred for 2 hours at room temperature, poured onto ice/water (50 g) and filtered, washed with brine and water, dried (MgSO$_4$), and evaporated under reduced pressure to a yellow oil (1.62 g). This was purified by flash chromatography on silica gel eluted with petroleum ether/ethyl acetate to give a yellow solid (0.98 g, 55%), m.p. 26–28° C.
Found: C, 63.9; H, 6.3; N,6.6%; $C_{11}H_{13}NOS$ requires: C, 63.7; H, 6.3; N, 6.8%

Examples 81 and 82 were by the same method used for Examples 5 and 6.

EXAMPLE 81

4-Methylsulphinyl-1-benzyl-azetidin-2-one

Colourless waxy solid
$^1$H NMR (CDCl$_3$)δ:2.38 (3H, s, SOCH$_3$), 2.49 (3H, s, SOCH$_3$), 2.84 (1H, dd, J=15.0, 2.25 Hz, H$_{3a}$), 3.09 (1H, dd, J=14.75, 4.75 Hz, H$_{3b}$), 3.22 (1H, dd, J=15.0, 5.25 Hz, H$_{3b}$), 3.52 (1H, dd, J=14.75, 2.50 Hz, H$_{3a}$), 4.22 (1H, m, H$_4$), 4.27, 4.78 (each 1H, d, J=15.0 Hz, N—CH$_2$), 4.35 (1H, m, ), 4.41, 4.85 (each 1H, d, J=15.0 Hz, N—CH$_2$), 7.20–7.42 (10H, m, Ph-H).
Found: C, 59.0; H, 5.8; N, 6.1%; $C_{11}H_{13}NO_2S$ requires: C, 59.2; H, 5.9; N, 6.3%

EXAMPLE 82

4-Methylsulphonyl-1-benzyl-azetidin-2-one

Colourless solid, m.p. 74–76° C.
Found: C, 55.2; H, 5.5; N, 5.9%; $C_{11}H_{13}NO_3S$ requires: C, 55.2; H, 5.5; N, 5.9%

EXAMPLE 83

4-Methylthio-1-(4-phenyl butyl)-azetidin-2-one

Substituting 4-phenyl-1-iodobutane (1.4 g, 5.5 mol) for benzyl bromide and increasing the reaction time to 24h and using appropriate molar quantities of the other reagents in Example 80 gave the title compound as a colourless oil, 0.59 g, 43%.
$^1$H NMR (CDCl$_3$)δ:1.63 (4H, m, CH$_2$CH$_2$), 1.99 (3H, s, SCH$_3$), 2.65 (2H, m, CH$_2$Ph), 2.92 (1H, dd, J=1.9, 15 Hz, H$_{3a}$), 3.03, 3.42 (each 1H, m, N—CH$_2$), 3.26 (1H, dd, J=5, 15 Hz, H$_{3b}$), 4,56 (1H, m, H$_4$), 7.15–7.31 (5H, m, Ph-H)

Examples 84 and 85 were by the same method used for Examples 5 and 6.

EXAMPLE 84

4-Methylsulfinyl-1-(4-phenylbutyl)-azetidin-2-one

Colourless oil, 83% yield
$^1$H NMR (CDCl$_3$)δ:1.6–1.8 (4H, m, CH$_2$), 2.45, 2.54 (3H, 2×s, SOCH$_3$), 2.65 (2H, m, CH$_2$Ph), 2.6–3.6 (4H, m, H3, NCH$_2$), 4.27,4.37 (1H, 2×m, .H), 7.1–7.3 (5H, m, Ph-H)

EXAMPLE 85

4-Methylsulfonyl-1-(4-phenyl butyl)-azetidin-2-one

Colourless solid, m.p. 59–60° C. 9% yield
Found: C, 59.73; H, 6.89; N, 4.75; $C_{14}H_{19}NO_3S$ requires: C, 59.76; H, 6.81; N, 4.98%

Examples 86–88 were prepared by methods analogousto those used in Examples 80, 5 and 6.

EXAMPLE 86 trans-3-Methyl-4-methylthio-1-(6-phenylhexyl)
azetidin-2-one

Colourless oil, 48% yield
Found: C, 69.72; H, 8.52; N, 4.39; S, 10.84; $C_{17}H_{25}NOS$ requires: C, 70.06; H, 8.65; N, 4.81; S, 11.00%

EXAMPLE 87 trans-3-Methyl-4-methylsulphinyl-1-(6-phenylhexyl)
azetidin-2-one

Pale yellow oil
$^1$H NMR (CDCl$_3$)δ:1.25–1.34 (12H, m, 2×CH$_2$CH$_2$CH$_2$), 1.39 (3H, d, J=7.5 Hz, CHCH$_3$), 1.45 (3H, d, J=7.5 Hz, CHCH$_3$), 1.62–1.67 (4H, m, 2×NCH$_2$CH$_2$), 2.51 (3H, s, SOCH$_3$), 2.55(3H, s, SOCH$_3$), 2.60(4H, t, J=7.25 Hz, 2×CH$_2$Ph), 2.98 (1H, dd, J=2.5, 7.5 Hz, H$_3$), 3.22–3.52 (4H, m, 2×N—CH$_2$), 3.69 (1H, q, J=2.5, 7.5 Hz, H$_3$), 4.00 (1H, d, J=2.5 Hz, H$_4$), 4.08 (1H, d, J=2.5 Hz, H$_4$), 7.14–7.30 (10H, m, Ph-H).

EXAMPLE 88 trans 3-Methyl-4-methylsulphonyl-1-(6-phenylhexyl)azetidin-2-one

Colourless solid, m.p. 72–73° C., 26% yield
Found: C, 63.0; H, 7.7; N, 4.3%; $C_{17}H25NO_3S$ requires: C, 63.1; H, 7.8; N, 4.3%

EXAMPLE 89

6-(4-Fluorophenyl)hexyl trans 3-methyl-4-methylthio-2-oxo-azetidin-1-ylacetate

Treatment of 4-methylthio-2-oxo-azetidin-1-ylacetic acid with (4-fluorophenyl)hexanol in the presence of diethylazodicarboxylate and triphenyl 30 phosphine gave the title compound as a colourless oil, 34% yield
Found: C, 62.3; H, 7.1; N, 3.5%; $C_{19}H_{26}FNO_3S$ requires: C, 62.1; H, 7.1; N, 3.8%

EXAMPLE 90

4-(2-Hydroxyethylthio)-N-(4-phenyl-2-oxobutyl)azetidin-2-one a. 4-(2-hydroxyethyl thio)azetidin-2-one
4-(2-Hydroxyethylthio)azetidin-2-one was prepared from 2-hydroxyethylthiol and 4-acetoxyazetidinone by the procedure described in Example 16 A and was isolated as a colourless oil, 3.4 g, 46% yield
$^1$H NMR δ (CDCl$_3$) 2.79–2.92 (3H, m, O-CH$_2$ and H$_{3a}$), 3.34–3.43 (1H, m, H$_{3b}$), 3.77–3.82 (1H, m, S-CH$_2$), 3.89–3.96 (1H, m, S-CH$_2$), 4.80–4.84 (1H, m, H$_4$), 6.88 40 (1H, br. singlet, N-H).
b. 4-(2-hydroxyethylthio)-N-(4-phenyl-2-oxobutyl)azetidin-2-one Treatment of 4-(2-hydroxyethylthio)azetidin-2-one with 1-bromo-4-phenylbutan-2-one in the presence of NaH in THF gave the title compound as a colourless oil, 1.4 g, 50% yield
$^1$H NMR δ (CDCl$_3$) 2.64–2.70 (2H, m, Ph-CH$_2$), 2.73–2.80 (2H, m,CO—CH$_2$), 2.90–2.96 (2H, m, O—CH$_2$), 3.00 (1H, dd, J=15.24,2.20 Hz, H$_{3a}$), 3.50 (1H, dd, J=15.16, 4.95 Hz, H$_{3b}$), 3.66–3.79 (3H, m, S—CH$_2$, N—CH$_2$), 4.27 (1H, d, J=18.41 Hz, N—CH$_2$), 4.94 (1H, dd, J=5.05, 2.36 Hz, H$_4$), 7.16–7.33 (5H, m, Ph-H).

EXAMPLE 91

4-(2-Hydroxyethylsulphinyl)-N-(4-phenyl-2-oxobutyl)azetidin-2-one (86% Diastereoisomer 1)

Treatment of 4-(2-hydroxyethylthio)-N-(4-phenyl-2-oxobutyl)azetidin-2-one with mCPBA as described for Example 17 gave the title compound by crystallisation: white crystals, m.p. 104–5° C., 20% yield
$^1$H NMR δ (CDCl$_3$) 2.54 (1H, br. triplet, J=5.03 Hz, O—H), 2.68–2.84 (4H, m, CH$_2$), 2.89–2.95 (2H, m, CH$_2$), 3.26 (1H, dd, J=14.82, 4.83 Hz, H$_{3a}$), 3.59 (1H, dd, J=14.80, 1.75 Hz, H$_{3b}$), 3.89 and 4.45 (1H each d, J=18.88 Hz, N—CH$_2$), 4.11–4.18 (2H, m, SO—CH$_2$), 4.85 (1H, dd, J=4.82, 2.18 Hz H$_4$), 7.15–7.36 (5H, m, Ph-H).
Found: C, 57.7; H, 6.1; N, 4.6%; $C_{15}H_{19}NO_4S$ 0.1H$_2$O requires: C, 57.9; H, 6.2; N, 4.5%

EXAMPLE 92

4-(2-Hydroxyethylsulphinyl)-N-(4-phenyl-2-oxobutyl)azetidin-2-one (Diastereoisomer 2)

The title compound was obteined from the mother liquors of the recrystallication carried out in Example 91 and was obteined as white crystals, m.p. 64–5° C., 20% yield
$^1$H NMR δ (CDCl$_3$) 2.52 (1H, t, J=5.01 Hz, O—H), 2.71–2.79 (2H, m, Ph-CH$_2$), 2.81–2.87 (2H, m, SO—CH$_2$), 2.88–2.99 (3H, m, CO—CH$_2$, H$_{3a}$), 3.41 (1H, dd, J=15.15, 5.19 Hz, H$_{3b}$), 4.11–4.20 (2H, m, O—CH$_2$), 4.22 and 4.43 (1H each, d, J=18.71 Hz, N—CH$_2$), 4.95 (1H, dd, J=5.18, 2.43 Hz, H$_4$), 7.15–7.33 (5H, m, Ph-H).
Found: C, 58.3; H, 6.0; N, 4.8%; $C_{15}H_{19}NO_4S$ requires: C, 58.2; H, 6.2; N, 4.5%
Examples 93 and 94 were prepared by the methods used for Examples 90 and 91.

EXAMPLE 93

4-(Methoxycarbonylmethylthio)-N-(4-phenyl-2-oxobutyl)azetidin-2-one a. 4-(Methoxycarbonylmethylthio)azetidin-2-one
Purple oil, 25% yield
$^1$H NMR δ (CDCl$_3$) 2.90 (1H, dd), 3.37 (2H, s), 3.40 (1H, dd), 3.76 (3H, s), 4.85 (1H, m), 6.65 (broad)
b. 4-(Methoxycarbonylmethylthio)-N-(4-phenyl-2-oxobutyl)azetidin-2-one
$^1$H NMR δ (CDCl$_3$) 2.76 (2H, m), 2.92 (2H,m), 3.07 (1H, dd), 3.26 (2H, s), 3.52 (1H, dd), 3.72 (3H,s), 3.83 and 4.25 (each 1H, d), 4.98 (1H, dd,), 7.16–7.32 (5H, m)

EXAMPLE 94

4-(methoxycarbonylmethylsulfinyl)-N-(4-phenyl-2-oxobutyl)azetidin-2-one (Diastereoisomer 1)

White crystalline solid, m.p. 137–39° C., 31% yield
Found: C, 56.71; H, 5.57; N, 4.26%; $C_{16}H_{19}NO_5S$ requires: C, 56.96; H, 5.68; N, 4.15%

EXAMPLE 95

N-[6-(4-Fluorophenyl)hexyl]-[4-(3-allyloxycarbonylpropyl)thio-2-oxo-azetidin-1-yl]-acetamide a. Allyl 4-bromobutanoate
4-Bromobutryl chloride (18.6 g) was treated with allyl alcohol (5.8 g) in the presence of pyridine (8 g) in dry dichloromethane at 0° C. for 0.5 hours. The solution was treated with aqueous HCl and warmed to room temperature. The organic layer was separated, washed with saturated aqueous brine, dried (MgSO$_4$) and evaporated to give the title compound as a colourless oil, 19.7 g, 95% yield
$^1$H NMR δ (CDCl$_3$) 2.2 (m, 1×CH$_2$), 2.54 (2H, t), 3.35 (2H, m), 4.60 (2H, m), 5.29 (2H, m), 5.94 (1H, m)

b. Allyl 4-(acetylthio)butanoate

Allyl 4-bromobutyrate (19.7 g) was treated with potassium thioacetate (10.9 g) in dimethyl formamide (100 ml) at 20° C. for 2 hours. Water (500 ml) was added and the mixture extracted with diethyl ether. The ethereal solution was washed with dilute aq. HCl, brine, dried (MgSO$_4$) and evaporated to give the title compound as an oil (18.6 g, 97%)
$^1$H NMR δ (CDCl$_3$) 1.9 (m, 1×CH$_2$), 2.32 (3H, s), 2.42 (2H, t), 2.92 (2H, t), 3.35 (2H, m), 4.60 (2H, m), 5.29 (2H, m), 5.94 (1H, m)

c. 4-(3-Allyloxycarbonylpropylthio)azetidin-2-one

Sodium (1.15 g) was added to allyl alcohol (50 ml) and this solution treated with allyl 4-(acetylthio)butanoate (10.0g) at room temperature for 20 mins. 4-Acetoxyazetidinone (6.5 g) was added and stirring continued at 20° C. for 1 h The resulting mixture was poured into excess ethyl acetate and the layers separated. The organic layer was washed with water, brine, dried (MgSO$_4$), filtered and evaporated. The residue was chromatographed on silica gel (diethyl ether) to give the title compound as a yellow oil, 5.5 g. 48% yield
$^1$H NMR δ (CDCl$_3$) 2.50 (2H, m), 2.7 (2H, t), 2.92 (1H, dd), 3.4 (1H, dd), 4.59 (2H, dd), 4.8 (1H, m), 5.23–5.37 (2H, m), 5.9 (1H, m), 6.5 (1H, broad)

d. N-[6-(4-Fluorophenyl)hexyl]-1-bromoacetamide

A cooled solution of 6-(4-fluorophenyl)hexylamine (2.0 g) and Hunig's base (1.33 g) in dry dichloromethane (25 ml) was treated with bromoacetylbromide (2.07 g) in dichloromethane (10 ml) at 0–5° C. After workup and chromatography N-[6-(4-fluorophenyl)hexyl]-1-bromoacetamide was obtained as a colourless solid, 2.71 g, m.p.50–51° C.

e. N-[6-(4-Fluorophenyl)hexyl]-[4-(3-allyloxycarbonylpropyl)thio-2-oxo-azetidin-1-yl]-acetamide 4-(3-Allyloxycarbonylpropylthio)azetidin-2-one (5.5 g) was treated with the above bromoacetamide (7.6 g) in dry THF in the presence of potassium t-butoxide (2.7 g) and 18-crown-6 (5mg) at –40 to –30° C. for 2 hours. Aqueous work-up followed by silica gel chromatography (diethyl ether and then EtOAc) gave the title compound as a colourless oil, 2.34 g, 21% yield
$^1$H NMR δ (CDCl$_3$) 1.30–1.60 (m, 4×CH$_2$), 1.95 (2H, m), 2.46 (2H, t), 2.58 (2H, t), 2.65 (2H, m), 2.97 (1H, dd), 3.24 (2H, m) 3.48 (1H,dd), 3.7–4.0 (2H, q), 4.6 (2H, m),4.90 (1H, dd), 5.23–5.34 (2H, m), 5.9 (1H, m), 6.9–7.1 (4H, m)

EXAMPLE 96

N-[6-(4-Fluorophenyl)hexyl]-[4-(3-allyloxycarbonylpropyl)sulphinyl-2-oxo-azetidin-1-yi]-acetamide (Diastereomer 1)

Treatment of N-[6-(4-Fluorophenyl)hexyl]-[4-(3-allyloxycarbonylpropyl)thio-2-oxo-azetidin-1-yl]-acetamide with mCPBA as described for Example 17 gave thetitle compound as a white crystalline solid, m.p. 95–96° C., 21% yield
Found: C, 59.68; H, 6.71; N, 5.75%; C$_{24}$H$_{33}$FN$_2$O$_5$S requires: C, 59.98; H, 6.92; N, 5.83%

EXAMPLE 97

N-[6-(4-Fluorophenyl)hexyl]-[4-(3-allyloxycarbonylpropyl)sulphinyl-2-oxo-azetidin-1-yl]-acetamide (Diastereomer 2)

Evaporation of the filtrate from crystallisation of Example 96 from the mixture of diastereoisomers gave the title compound (diastereoisomer 2) as a brown oil, 51% yield Found: C, 57.4; H, 6.5; N, 5.7%; C$_{24}$H$_{33}$FN$_2$O$_5$S 0.3CH$_2$Cl$_2$ requires: C, 57.67; H, 6.69; N, 5.54%

EXAMPLE 98

N-[6-(4-Fluorophenyl)hexyl]-[4-(3-carboxypropyl) thio-2-oxo-azetidin-1-yl]-acetamide N-[6-(4-Fluorophenyl)hexyl]-[4-(3-allyloxycarbonylpropyl)thio-2-oxo-azetidin-1-yl]-acetamide (1.4 g) was dissolved in dry dichloromethane (30 ml) and the resulting solution treated with pyrrolidine (0.3 g) and (tetrakistriphenylphosphino)palladium (0.2 g) at room temperature until TLC analysis showed absence of starting material. The mixture was washed with dilute HCl, brine, dried (MgSO$_4$) and evaporated. The residue was purified by chromatography on silica gel (dichloromethane:methanol:acetic acid, 90:9:1) to give the title compound as an oil, 0.7 g, 52% yield.
$^1$H NMR δ (CDCl$_3$) 1.30–1.60 (m, 4×CH$_2$), 1.93 (2H, m), 2.6 (6H, m), 3.0 (1H, dd), 3.20 (2H, m), 3.42 (1H, dd), 3.75–4.0 (2H, q), 4.9 (1H, dd), 6.4 (1H, broad m), 6.9–7.1 (4H, m)

EXAMPLE 99

N-[6-(4-Fluorophenyl)hexyl]-[4-(3-carboxypropyl) sulphinyl-2-oxo-azetidin-1-yl]-acetamide (Diastereoisomer 1)

Synthesis: Oxidation using ozone

Ozonised oxygen was bubbled through a solution of N-[6-(4-fluorophenyl)hexyl]-[4-(3-carboxypropyl)thio-2-oxo-azetidin-1-yl]-acetamide (0.7 g) in dry dichloromethane (30 ml) at -70° C. until all starting material had been consumed. Excess ozone was purged with oxygen, the reaction mixture allowed to warm to room temperature and evaporated to dryness. Tituration with ether gave a soild which was recrystallised from ethyl acetate to give the title compound as off white crystals, 0.4 g, m.p. 85–7° C., 53% yield (recryst of mother liquors etc)
Found: C, 54.0; H, 6.5; N, 6.1%; C$_{21}$H$_{29}$FN$_2$O$_5$S 0.4H$_2$O requires: C, 54.2; H, 6.9; N, 6.0%

EXAMPLE 100

N-[6-(4-Fluorophenyl)hexyl]-[4-(3-carboxypropyl) sulphinyl-2-oxo-azetidin-1-yl]-acetamide (Diastereoisomer 2)

Evaporation of the filtrate from crystallisation of Example 99 and chromatography of the residue on silica gel (dichloromethane:methanol:acetic acid, 90:9:1) gave the title compound as a viscous colourless oil, 0.16 g, 23% yield
Found: C, 52.8; H, 6.2; N, 5.5%; C$_{21}$H$_{29}$FN$_2$O$_5$S 0.64H$_2$O requires: C, 52.5; H, 6.2; N, 5.7%

The compounds in Examples 101 and 102 were prepared by process described for the analogous compounds in Examples 95.

EXAMPLE 101

N-[6-(4-Fluorophenyl)hexyl]-[4-methoxycarbonylmethylthio-2-oxo-azetidin-1-yl]-acetamide Colourless oil, 25% yield
$^1$H NMR δ (CDCl$_3$) 1.30–1.60(m,4×CH$_2$),2.55(2H,t),3.0 (1H, dd), 3.2–3.5 (5H, m), 3.7–4.1(5H, m), 5.0 (1H, dd), 6.6 (1H, broad), 6.9–7.1 (4H, m)

EXAMPLE 102

N-[6-(4-Fluorophenyl)hexyl]-[4-allyloxycarbonylmethylthio-2-oxo-azetidin-1-yl]-acetamide a. 4-Allyloxycarbonylmethylthio-azetidin-2-one
Yellow oil, 73% yield
$^1$H NMR δ (CDCl$_3$) 2.90 (1H, dd), 3.37 (2H, s), 3.40 (1H, dd), 4.6 (2H, m), 4.88 (1H, dd), 5.33 (2H, m), 5.9 (1H, m), 6.5 (1H, broad)

b. N-[6-(4-Fluorophenyl)hexyl]-[4-allyloxycarbonylmethylthio-2-oxo-azetidin-1-yl]-acetamide Colourless oil, 30% yield
$^1$H NMR δ (CDCl$_3$) 1.30–1.60(m, 4×CH$_2$), 2.55(2H, t), 3.0–3.5 (6H, m), 3.7–3.9(2H, q), 4.6(2H, m) 5.0 (1H, dd), 5.3(2H, m), 5.8–6.0 (2H, m), 6.9–7.1 (4H, m)

The compounds in Examples 103 and 104 were prepared from N-[6-(4-fluorophenyl)hexyl]-[4-carbemethoxymethylthio-2-oxo-azetidin-1-yl]-acetamide by the process described for the analogous compounds in Examples 17 and 18.

EXAMPLE 103

N-[6-(4-Fluorophenyl)hexyl]-[4-methoxycarbonylmethylsulphinyl-2-oxo-azetidin-1-yl]-acetamide (Diastereoisomer 1)

White crystalline solid, m.p. 131–33° C., 21% yield
Found: C, 56.3; H, 6.3; N, 6.6%; C$_{20}$H$_{27}$FN$_2$OS requires: C, 56.3; H, 6.4; N, 6.6%

EXAMPLE 104

N-[6-(4-Fluorophenyl)hexyl]-[4-methoxycarbonylmethylsulphinyl-2-oxo-azetidin-1-yl]-acetamide (Diastereomer 2)

Form Off white solid, m.p.90–93° C., 57% yield
Found: C, 56.6; H, 6.2; N, 6.8%; C$_{20}$H$_{27}$FN$_2$O$_5$S requires: C, 56.3; H, 6.4; N, 6.6%

EXAMPLE 105

N-[6-(4-Fluorophenyl)hexyl]-[4-carboxymethylthio-2-oxo-azetidin-1-yl]-acetamide

The title compound was prepared from N-[6-(4-fluorophenyl)hexyl]-[4-allyloxycarbonylmethylthio-2-oxo-azetidin-1-yl]-acetamide using the procedure described for Example 98 and was isolated as a colourless oil, 78% yield
$^1$H NMR δ (CDCl$_3$) 1.30–1.60 (m, 4×CH$_2$), 2.55 (2H, t), 3.0–4.0 (9H, m), 5.0 (1H, dd), 6.6 (1H, m), 6.9–7.1 (4H, m)

Treatment of N-[6-(4-fluorophenyl)hexyl]-[4-carboxymethylthio-2-oxo-azetidin-1-yl]-acetamide with ozone as described for Examples 99 and 100 gave the compounds described in Examples 106 and 107 below.

EXAMPLE 106

N-[6-(4-Fluorophenyl)hexyl]-[4-carboxymethylsulphinyl-2-oxo-azetidin-1-yl]-acetamide (Diastereolsomer 1)

Off white crystals, m.p. 134–36° C., 20% yield
Found: C, 53.7; H, 5.8; N, 6.8%; C$_{19}$H$_{13}$FN$_2$O$_5$S 0.8H$_2$O requires: C, 53.7; H, 5.8; N, 6.6%

EXAMPLE 107

N-[6-(4-Fluorophenyl)hexyl]-[4-carboxymethylsulphinyl-2-oxo-azetidin-1-yl]-acetamide (Diastereoisomer 2)

Off white crystals, m.p. 93–96° C., 14% yield
Found: C, 54.4; H, 5.8; N, 6.7% C$_{19}$H$_{23}$FN$_2$O$_5$S 0.5H$_2$O requires: C, 54.4; H, 5.8; N, 6.7%

Biological Data

1. Screen for Lp-PLA$_2$ inhibition.

Enzyme activity was determined by measuring the rate of turnover of the artificial substrate (A) at 37° C. in 50 mM HEPES (N-2-hydroxyethylpiperazine-N'-2-ethanesulphonic acid) buffer containing 150 mM NaCl, pH 7.4.

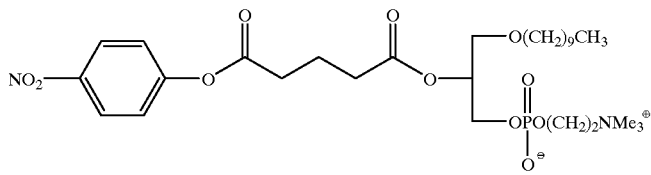

(A)

Assays were performed in 96 well titre plates.

Lp-PLA$_2$ was partially purified by density gradient centrifugation of human plasma. Active fractions were pooled and used as the source of Lp-PLA$_2$. The enzyme was pre-incubated at 37° C. with vehicle or test compound for 10 min in a total volume of 180 μl. The reaction was then initiated by the addition of 20 μl 10× substrate (A) to give a final substrate concentration of 20 μM. The reaction was followed at 405 nm for 20 minutes using a plate reader with automatic mixing. The rate of reaction was measured as the rate of change of absorbance.

Results:

The compounds of Example 18, 21, 24, 63, 71, 79 and 84 had IC$_{50}$ values in the range 0.03 to 0.40 μM.

2. Inhibition of Cu 2+stimulated lyso-phosphatidylcholine (lyso-PtdCho) formation.

A 1 ml aliquot of human LDL (0.25 mg protein/ml) was incubated for 15 min at 37° C. with compound or vehicle. 5 μM Cu$^{2+}$ was then added to allow oxidation/lyso-PtdCho formation to occur. The incubation was terminated by the addition of 3.75 ml chloroform/methanol/c HCl (200:400:5, v/v/v). Following the addition of 1.25 ml chloroform and 1.25 ml 0.1M HCl, the mixture was vortexed and centrifuged. The lower phase was carefully removed and the upper phase re-extracted with an equal volume of synthetic lower phase. The extracts were pooled and dried under nitrogen.

Phospholipids were reconstituted into 50 μl chloroform/methanol (2:1 v/v). 10 μl aliquots were spotted on to pre-run silica gel HPTLC plates and then developed in chloroform/methanol 25–30% methylamine (60:20:5 v/v/v). Plates were subsequently sprayed with the flourescent indicator, 2-p-toluidinylnaphthalene-6-sulphonic acid (1 mM in 50 mM Tris/HCl, pH 7.4) to identify phospholipid components. Fluorescence was measured at 222 nm using a CAMAG TLC scanner. Lipoprotein lyso-PtdCho content was quantified using a standard curve (0.05–0.5 µg) prepared in parallel.

Compound 71 dose dependently inhibits LDL lyso-PtdCho accumulation stimulated by copper ions with an $IC_{50}$ value of ~0.06 µM.

We claim:

1. A compound of formula (I):

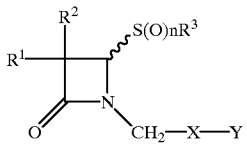

in which:

$R^1$ and $R^2$, which may be the same or different, is each selected from hydrogen or $C_{(1-8)}$alkyl;

$R^3$ is $C_{(1-8)}$alkyl or $C_{(3-8)}$cycloalkyl each of which may be optionally substituted by halo, hydroxy, and $CO_2R$ in which R is hydrogen, $C_{(1-8)}$alkyl, $C_{(2-8)}$alkenyl or an in vivo hydrolysable ester group;

X is a direct bond; a group $X'(CH_2)m$ in which X' is CO, $CONR^5$, COO or C(O)NH—O— in which $R^5$ is hydrogen or $C_{(1-6)}$alkyl and m is 0 or an integer from 1 to 8; or a $C_{(1-12)}$alkylene chain optionally interupted by X';

Y is phenyl optionally substituted by halogen, cyano, $(C_{1-6})$alkyl, $(C_{3-7})$cycloalkyl, $(C_{1-6})$alkoxy, halo$(C_{1-6})$alkyl, hydroxy, amino, mono- or di-$(C_{1-6})$alkylamino, nitro, carboxy, $(C_{1-6})$alkoxycarbonyl, $(C_{1-6})$alkoxycarbonyl$(C_{1-6})$alkyl, $(C_{1-6})$alkylcarbonyloxy, carboxy$(C_{1-6})$alkyloxy, $(C_{1-6})$alkylcarbonyloxy, $(C_{1-6})$alkylthio, $(C_{1-6})$alkylsulphinyl, $(C_{1-6})$alkylsulphonyl, sulphamoyl, mono- and di-$(C_{1-6})$-alkylsulphamoyl, carbamoyl, mono- and di-$(C_{1-6})$alkylcarbamoyl;

m is 0 an integer from 1 to 12; and n is 1 or 2.

2. A compound as claimed in claim 1 in which $R^1$ and $R^2$ is each selected from hydrogen, methyl or ethyl.

3. A compound as claimed in claim 1 in which $R^1$ and $R^2$ is each hydrogen or one of $R^1$ and $R^2$ is hydrogen and the other of $R^1$ and $R^2$ is methyl.

4. A compound as claimed in claim 1 in which $R^3$ is n-butyl, t-butyl or n-hexyl or $C_{(1-8)}$alkyl substituted by $CO_2R$ in which R is hydrogen or an in vivo hydrolysable ester group.

5. A compound as claimed in claim 1 in which n is 1.

6. A compound as claimed in claim 1 in which X' is CO or $CONR^5$.

7. A compound as claimed in claim 1 in which m is 1, 5, 6 or 7.

8. A compound as claimed in claim 1 in which X is $CONH(CH_2)_6$.

9. A compound as claimed in claim 1 in which Y is phenyl optionally substituted by halo.

10. A compound of formula (I) as defined in claim 1 selected from:

4-Methylsulphinyl-1-(4-phenyl-2-oxobutyl)azetidin-2-one;

4-Methylsulphonyl-1-(4-phenyl-2-oxobutyl)azetidin-2-one;

4-Methylsulphinyl-1-(9-phenyl-2-oxononyl)azetidin-2-one;

4-Methylsulphonyl-1-(9-phenyl-2-oxononyl)azetidin-2-one;

4-Methylsulphinyl-1-phenacylazetidin-2-one;

4-Methylsulphonyl-1-phenacylazetidin-2-one;

4-Methylsulphinyl-1-(5-phenyl-2-oxopentyl)azetidin-2-one;

4-Methylsulphonyl-1-(5-phenyl-2-oxopentyl)azetidin-2-one;

4-Methylsulphinyl-1-(7-phenyl-2-oxoheptyl)azetidin-2-one;

4-Methylsulphonyl-1-(7-phenyl-2-oxoheptyl)azetidin-2-one;

4-Butylsulfinyl-1-(4-phenyl-2-oxobutyl)azetidin-2-one, (diastereoisomer 1);

4-Butylsulfinyl-1-(4-phenyl-2-oxobutyl)azetidin-2-one, (distereoisomer 2);

4-Butylsulfonyl-1-(4-phenyl-2-oxobutyl)azetidin-2-one;

4-tert-Butylsulfinyl-1-(4-phenyl-2-oxobutyl)azetidin-2-one;

4-Hexylsulfinyl-1-(4-phenyl-2-oxobutyl)azetidin-2-one, (diastereoisomer 1);

4-Hexylsulfinyl-1-(4-phenyl-2-oxobutyl)azetidin-2-one, (diastereoisomer 2);

Benzyl (4-methylsulfinyl-2-oxo-azetidin-1-yl)acetate, (diastcreoisomer 1);

Benzyl (4-methylsulfinyl-2-oxo-azetidin-1-yl)acetate (diastereoisomer 2);

Benzyl (4-methylsulfonyl-2-oxo-azetidin-1-yl)acetate;

(+)-Benzyl (4-methylsulphonyl-2-oxoazetidin-1-yl) acetate;

(−)-Benzyl (4-methylsulphonyl-2-oxoazetidin-1-yl) acetate;

trans-Benzyl (3-methyl-4-methylsulphinyl-2-oxoazetidin-1-yl)acetate;

trans-Benzyl (3-methyl-4-methylsulphonyl-2-oxoazetidin-1-yl)acetate;

4-Methylsulphinyl-1-(4-phenyl-4-oxobutyl)azetidin-2-one;

cis-Benzyl (3-methyl-4-methylsulphinyl-3-oxoazetidin-1-yl)acetate;

Benzyl (3,3-dimethyl-4-methylsulphonyl-2-oxoazetidin-1-yl)acetate;

Benzyl (3,3-dimethyl-4-methylsulphinyl-2-oxoazetidin-1-yl)acetate;

Benzyl (3,3-diethyl-4-methylsulphinyl-2-oxoazetidin-1-yl)acetate;

Benzyl (3,3-diethyl-4-methylsulphonyl-2-oxoazetidin-1-yl)acetate;

N-(2-Phenylethyloxy)-(4-methylsulfinyl-2-oxo-azetidin-1-yl)acetamide;

N-(2-Phenylpropyloxy)-(4-methylsulfinyl-2-oxo-azetidin-1-yl)acetamide;

N-(2-Phenylpropyloxy)-(4-methylsulfonyl-2-oxo-azetidin-1-yl)acetamide;

(±)-N-Benzyl-(4-methylthio-2-oxoazetidin-1-yl) acetamide;

(±)-N-Benzyl-(4-methylsuphinyl-2-oxoazetidin-1-yl) acetamide;

N-Benzyl-(4-methylsuphonyl-2-oxoazetidin-1-yl) acetamide;

N-6-Phenylhexyl-(4-methylsulphinyl-2-oxoazetidin-1-yl) acetamide;

N-6-Phenylhexyl-(4-methylsulphonyl-2-oxoazetidin-1-yl)acetamide;

trans-N-Benzyl-(3-methyl-4-methylsulphinyl-2-oxoazetidin-1-yl)acetamide;

trans-N-benzyl-(3-methyl-4-methylsulphonyl-2-oxoazetidin-1-yl)acetamide;

cis-N-(6-Phenylhexyl)-(3-methyl-4-methylsulfinyl-2-oxoazetidin-1-yl)acetamide;

trans-N-(6-phenylhexyl)-(3-methyl-4-methylsulphinyl-2-oxoazetidin-1-yl)acetamide;

trans N-(6-Phenylhexyl)-(3-methyl-4-methylsulphonyl-2-oxoazetidin-1-yl)acetamide;

N-Benzyl-(3,3-dimethyl-4-methylsulphinyl-2-oxoazetidin-1-yl)acetamide, (diastereoisomer 2);

N-Benzyl-(3,3-dimethyl-4-methylsulphinyl-2-oxoazetidin-1-yl)acetamide, (diastereoisomer 1);

N-Benzyl-(3,3-dimethyl-4-methylsulphonyl-2-oxoazetidin-1-yl)acetamide;

N-(6-Phenylhexyl)-(4-n-hexylsulfinyl-2-oxoazetidin-1-yl)acetamide, (diastereoisomer 1);

N-(6-Phenylhexyl)-(4-n-hexylsulfinyl-2-oxoazetidin-1-yl)acetamide, (diastereoisomer 2);

4-Methylsulphinyl-1-benzyl-azetidin-2-one;

4-Methylsulphonyl-1-benzyl-azetidin-2-one;

4-Methylsulfinyl-1-(4-phenylbutyl)-azetidin-2-one;

4-Methylsulfonyl-1-(4-phenylbutyl)-azetidin-2-one;

trans-3-Methyl-4-methylsulphinyl-1-(6-phenylhexyl)azetidin-2-one;

trans 3-Methyl-4-methylsulphonyl-1-(6-phenylhexyl)azetidin-2-one;

4-(2-Hydroxyethylsulphinyl)-N-(4-phenyl-2-oxobutyl)azetidin-2-one (Diastereoisomer 1); 4-(2-Hydroxyethylsulphinyl)-N-(4-phenyl-2-oxobutyl)azetidin-2-one (Diastereoisomer 2);

4-(methoxycarbonylmethylsulfinyl )-N-(4-phenyl-2-oxobutyl)azetidin-2-one (Diastercoisomer 1);

N-[6-(4-Fluorophenyl)hexyl]-[4-(3-allyloxycarbonylpropyl)thio-2-oxo-azetidin-1-yl]-acetamide;

N-[6-(4-Fluorophenyl)hexyl]-[4-(3-allyloxycarbonylpropyl)sulphinyl -2-oxo-azetidin-1-yl]-acetamide (Diastereomer 1);

N-[6-(4-Fluorophenyl)hexyl]-[4-(3-allyloxycarbonylpropyl)sulphinyl -2-oxo-azetidin-1-yl]-acetamide (Diastereomer 2);

N-[6-(4-Fluorophenyl)hexyl]-[4-(3-carboxypropyl)thio-2-oxo-azetidin-1-yl]-acetamide;

N-[6-(4-Fluorophenyl)hexyl]-[4-(3-carboxypropyl)sulphinyl-2-oxo-azetidin-1-yl]-acetamide (Diastereoisomer 1);

N-[6-(4-Fluorophenyl)hexyl]-[4-(3-carboxypropyl)sulphinyl-2-oxo-azetidin-1-yl]-acetamide (Diastereoisomer 2);

N-[6-(4-Fluorophenyl)hcexyl]-[4-methoxycarbonylmethylthio-2-oxo-azetidin-1-yl]-acetamide;

N-[6-(4-Fluorophenyl)hexyl]-[4-methoxycarbonylmethylsulphinyl-2-oxo-azetidin-1-yl]-acetamide (Diastereoisomer 1);

N-[6-(4-Fluorophenyl)hexyl]-[4-methoxycarbonylmethylsulphinyl-2-oxo-azetidin-1-yl]-acetamide (Diastereomer 2);

N-[6-(4-Fluorophenyl)hexyl]-[4-carboxymethylsulphinyl-2-oxo-azetidin-1-yl]-acetamide (Diastereoisomer 1); and N-[6-(4-Fluorophenyl)hexyl]-[4-carboxymethylsulphinyl-2-oxo-azetidin-1-yl]-acetamide (Diastereoisomer 2);

in which 'diastereoisomer 1' refers to the R,R/S,S configuration and 'diastereoisomer 2' refers to the R,S/S,R configuration.

11. A pharmaceutical composition comprising a compound of formula (I) as defined in claim 1 and a pharmaceutically acceptable carrier.

12. A method of treating atherosclerosis which method comprises administering an effective amount of a compound of formula (I) as defined in claim 1 to a patient in need thereof.

13. A process for preparing a compound of formula (I) as defined in claim 1, which comprises:

(a) treating an azetidone of formula (II):

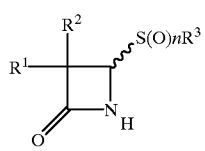

(II)

in which:

n, $R^1$, $R^2$ and $R^3$ are as hereinbefore defined;

with an alkylating agent of the formula (III):

ZCH$_2$XY   (III)

in which Z is a suitable leaving group; and

X and Y are as hereinbefore defined;

in the presence of a suitable base, in a suitable solvent, and at a temperature in the range −10 to 0° C.; and therafter, and if neccessary, for a compound in which n is 0, treating with an oxidising agent;

(b) for compounds of formula (1) in which X denotes a group X'(CH$_2$)m in which X' denotes CONR$^5$ (amide) or C(O)NH—O— (hydroxamate), treating an acid of the formula (IV):

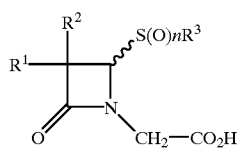

(IV)

in which:

n, m, $R^1$, $R^2$ and $R^3$ are as hereinbefore defined;

with an amine of the formula (V):

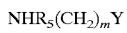

NHR$_5$(CH$_2$)$_m$Y   (V)

or hydroxylamine of the formula (VI):

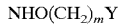

NHO(CH$_2$)$_m$Y   (VI)

in which Y and m are as hereinbefore defined, in the presence of an activating agent such as ethyl chloroformate or dicyclohexylcarbodiimide (DCC), in a suitable solvent such as chloroform or dimethyl formamide, at a temperature in the range −10 to 20° C.;

(c) for compounds of formula (I) in which X denotes a group X'(CH$_2$)$_m$ in which X' denotes COO (ester), by using a transesterification reaction from the methyl ester of formula (VII):

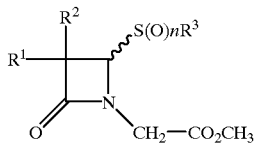
(VII)

in which:

n, m, R$^1$, R$^2$ and R$^3$ are as hereinbefore defined;

(d) for a compound of formula (I) in which X denotes a group X'(CH$_2$)$_m$ in which X' denotes COO (ester), treating a compound of formula (IV) with an alcohol Y(CH$_2$)$_m$OH or an activated derivative thereof;

in which m is as hereinbefore defined.

* * * * *